US007267815B2

(12) United States Patent
Ramesh et al.

(10) Patent No.: US 7,267,815 B2
(45) Date of Patent: Sep. 11, 2007

(54) METHODS AND REAGENTS FOR THE ENHANCEMENT OF VIRUS TRANSDUCTION IN THE BLADDER EPITHELIUM

(75) Inventors: Nagarajan Ramesh, Sunnyvale, CA (US); David Frey, Half Moon Bay, CA (US); Bahram Memarzadeh, San Carlos, CA (US); DeChao Yu, Foster City, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 82 days.

(21) Appl. No.: 10/743,813

(22) Filed: Dec. 24, 2003

(65) Prior Publication Data

US 2004/0176318 A1 Sep. 9, 2004

Related U.S. Application Data

(63) Continuation-in-part of application No. 10/327,869, filed on Dec. 26, 2002.

(51) Int. Cl.
*A61K 48/00* (2006.01)
*A61K 39/12* (2006.01)
*A61K 39/235* (2006.01)
*C12N 15/86* (2006.01)
*A01N 43/04* (2006.01)

(52) U.S. Cl. ............... 424/93.2; 424/204.1; 424/205.1; 424/233.1; 435/235.1; 435/456; 514/40

(58) Field of Classification Search ..................... None
See application file for complete search history.

(56) References Cited

U.S. PATENT DOCUMENTS

| | | | | |
|---|---|---|---|---|
| 5,368,844 | A | * 11/1994 | Gaffar et al. | .................. 424/49 |
| 5,369,095 | A | 11/1994 | Kee et al. | |
| 5,789,244 | A | * 8/1998 | Heidrun et al. | .......... 435/320.1 |
| 6,165,779 | A | 12/2000 | Engler et al. | |
| 2002/0169138 | A1 | 11/2002 | Kunz et al. | |

FOREIGN PATENT DOCUMENTS

| | | |
|---|---|---|
| JP | 1-245159 | 9/1989 |
| WO | WO97/25072 A1 | 7/1997 |
| WO | WO 02/40630 | * 5/2002 |

OTHER PUBLICATIONS

Zhang et al (Cancer Res. 62: 3743-3750, 2002).*
Mullen et al (Oncologist 7:106-119, 2002).*
Watanabe et al (Int. J. Cancer 92: 712-717, 2001).*
Connor et al (Gene Therapy 8: 41-48, 2001).*
Boer et al (Biochem. Biophys. Res. Comm. 166(1): 91-98, 1983).*
Sedzik et al (NeuroReport 11(11): 2559-2563, 2000).*
Derek Raghavan et al., "Biology and Management of Bladder Cancer", N. Engl. J. Med., 322, 16, pp. 1129-1138 (1990).

Simon F. Brewster et al., "Gene Therapy in Urological Oncology: Principles, Strategies and Potential", Eur. Urol. 25, pp. 177-182 (1984).
Rei Takahashi et al., "The retinoblastoma gene functions as a growth and tumor suppressor in human bladder carcinoma cells", Natl. Acad. Sci USA 88, pp. 5257-5261 (1991).
Steven A. Rosenberg, "The Immunotherapy and Gene Therapy of Cancer", J. Clin. Oncol., 10, pp. 180-199 (1992).
C. Bass et al., "Recombinant adenovirus-mediated gene transfer to genitourinary epithelium in vitro and in vivo", Cancer Gene Therapy 2, 2, pp. 97-104 (1995).
Bernard D. Morris, Jr. et al., "Adenoviral-Mediated Gene Transfer to Bladder in vivo", Urology, 152, pp. 506-550 (1994).
Y. Blixt et al., "Enhancement of intracellular uncoating of adenovirus in HeLa cells in the presence of benzyl alcohol as a membrane fluidizer", Virol., 129, pp. 265-277 (1993).
Frederick C. Monson et al., "Indigocarmine as a Quantitative Indicator of Urothelial Integrity", J. Urol., 145, pp. 842-845 (1992).
C.L. Parsons et al., "Bladder Surface Glycosaminoglycans: an Epithelial Permeability Barrier", J. Urol., 143, pp. 139-142 (1990).
D. Robert Siemens et al., "Evaluation of Gene Transfer Efficiency by Viral Vectors to Murine Bladder Epithelium", J. Urol., 165, pp. 667-671 (2001).
Mizamura, et al., "Plates for detection of antibodies to Newcastle disease virus and octyl-glucoside solubilization of virus antigen", Database CAPLUS on STN, No. 1990:115384, Abstract Only, 1990.
Zhang, et al., "Identification of Human Uroplakin II Promoter and Its Use in the Construction of CG8840, a Urothelium-specific Adenovirus Variant That Eliminates Established Bladder Tumors in Combination with Docetaxel", Cancer Research, vol. 62, pp. 3743-3750, 2002.
Connor, et al., "Identification of polyamides that enhance adenovirus-mediated gene expression in the urothelium", Gene Therapy, vol. 8, pp. 41-48, 2001.
Watanabe, et al,. "Adenovirus-Mediated Gene Therapy for Bladder Cancer in an Orthotopic Model Using a Dominant Negative H-*RAS* Mutant", Int. J. Cancer, vol. 92, pp. 712-717, 2001.
Mullen, et al., "Viral Oncolysis", The Oncologist, vol. 7, pp. 106-119, 2002.
Boer, et al., "Solubilization of Ligand-Stabilized Vasopressin Receptors from Plasma Membranes of Bovine Kidney and Rat Liver", Biochem. Biophys. Res. Comm., vol. 116, No. 1, pp. 91-98, 1983.

(Continued)

*Primary Examiner*—Richard Schnizer
(74) *Attorney, Agent, or Firm*—James F. Haley, Jr.; Ropes & Gray, LLP

(57) ABSTRACT

Agents and methods for enhancing recombinant virus transduction in the bladder epithelium are described. A first method involves contacting the luminal surface of the bladder with a composition comprising a transduction enhancing agent and an oncolytic virus. Alternatively, the luminal surface of the bladder can be contacted first with a pretreatment composition comprising a transduction enhancing agent and, subsequently, with a composition comprising an oncolytic virus. Bladder treatment compositions comprising a transduction enhancing agent and an oncolytic virus are also described.

18 Claims, 64 Drawing Sheets

OTHER PUBLICATIONS

Sedzik, et al., "Solubilization of PNS myelin membrane proteins by detergents", Membrane Biophysics and Biochemistry, vol. 11, No. 11, pp. 2559-2563, 2000.

Kirn, "Replication-selective oncolytic adenoviruses: virotherapy aimed at genetic targets in cancer", Oncogene, vol. 19, pp. 6660-6669, 2000.

Rangel, et al,. "Taxol and taxotere in bladder cancer: in vitro activity and urine stability", Cancer Chemother. Pharmacol., vol. 33, pp. 460-464, 1994.

Loughlin, et al., "The Use of Hydrogen Peroxide to Enhance the Efficacy of Doxorubicin Hydrocloride in a Murine Bladder Tumor Cell Line", H. Urology, vol. 165, pp. 1300-1304, 2001.

Supplementary partial European Search report for European patnet ppplication No. 03800237.4.

Connor, R.J., et al., "Identification of polyamides that enhance adenovirus-mediated gene expression in the urothelium", *Gene Therapy*, 2001, 8:41-48, MacMillian Press Ltd., Basingstoke, GB.

Zhang, J., et al., "Identification of human uroplakin II promoter and its use in the construction of CG8840, a urotherlium-specific adenovirus variant that eliminates established bladder tumors in combination with docetaxel", *Cancer Research*, Jul. 1, 2002, 62(13):3743-3750, American Association for Cancer Research, Baltimore, MD.

\* cited by examiner

15%

20%

25%

30%

40X

100X

40X

100X

40X

100X

40x

100x

40x

100x

40x

100x

FIG. 5A    FIG. 5B
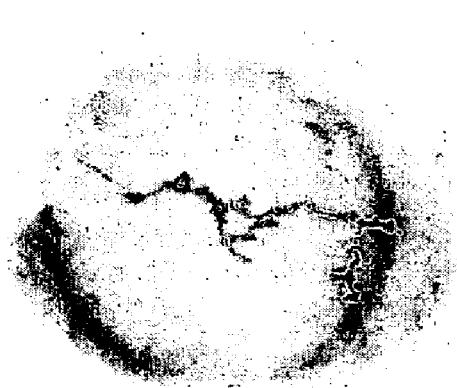
FIG. 5C    FIG. 5D

FIG. 7A  FIG. 7B
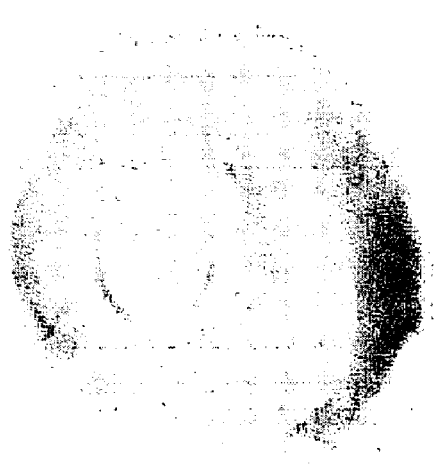
FIG. 7C  FIG. 7D

40x

100x

40x

100x

40x

100x

40x

100x

40x

100x

40x

100x

40x

100x

40x

100x

40x

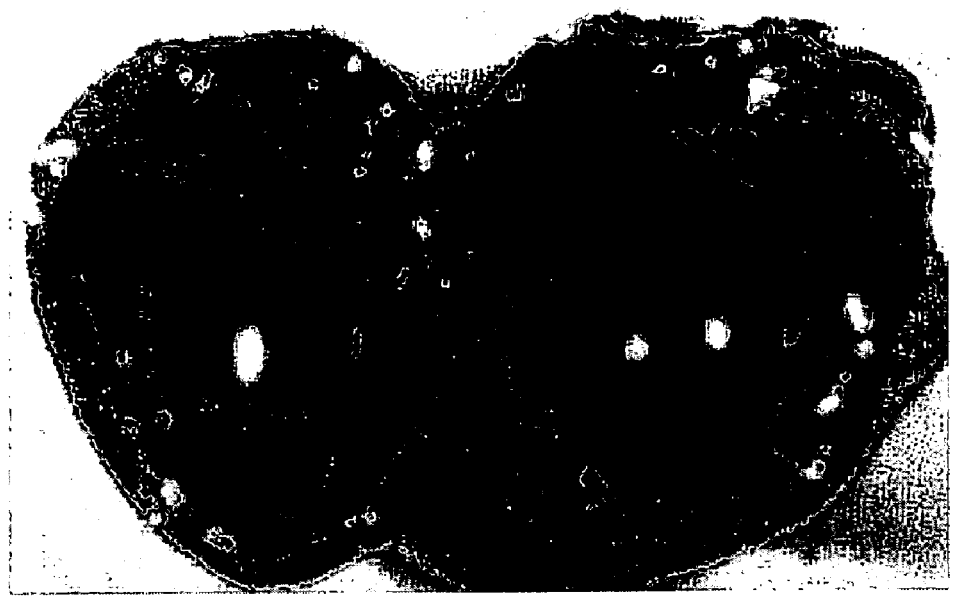
FIG. 17A
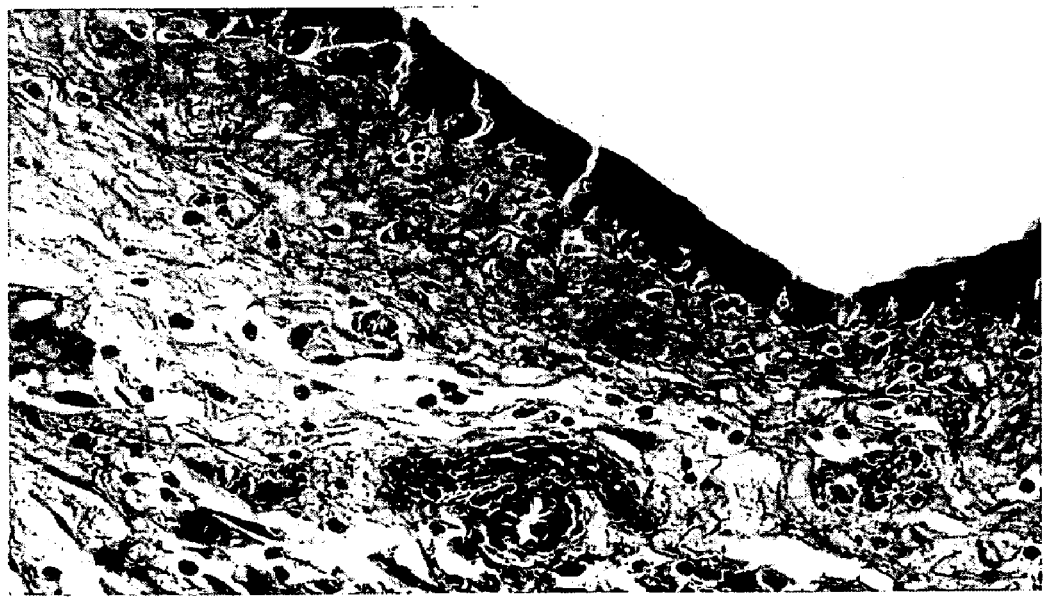
40x      FIG. 17B

100x

40x

40x

100x

40x

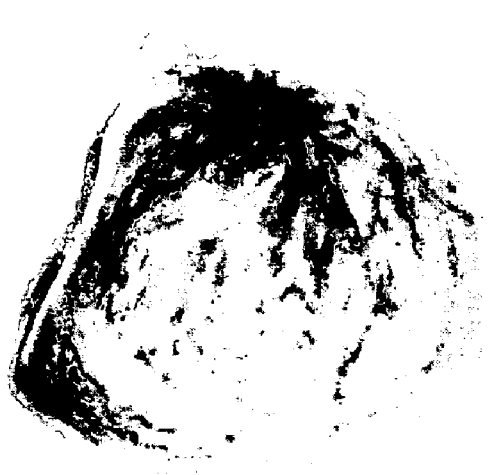
FIG. 21A  FIG. 21B
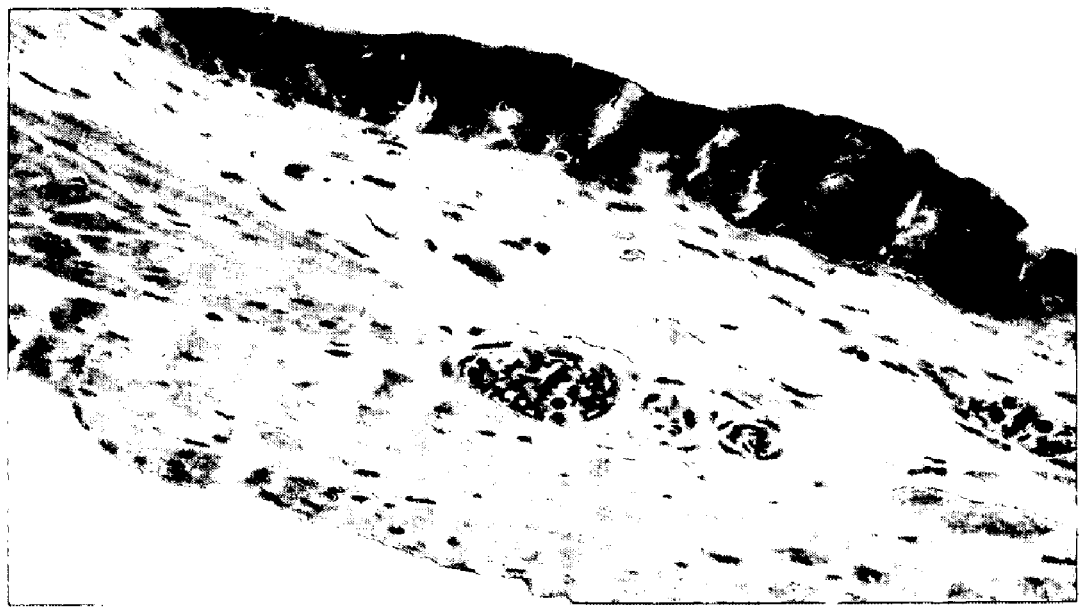
40x
FIG. 21C

100x

FIG. 22A  FIG. 22B
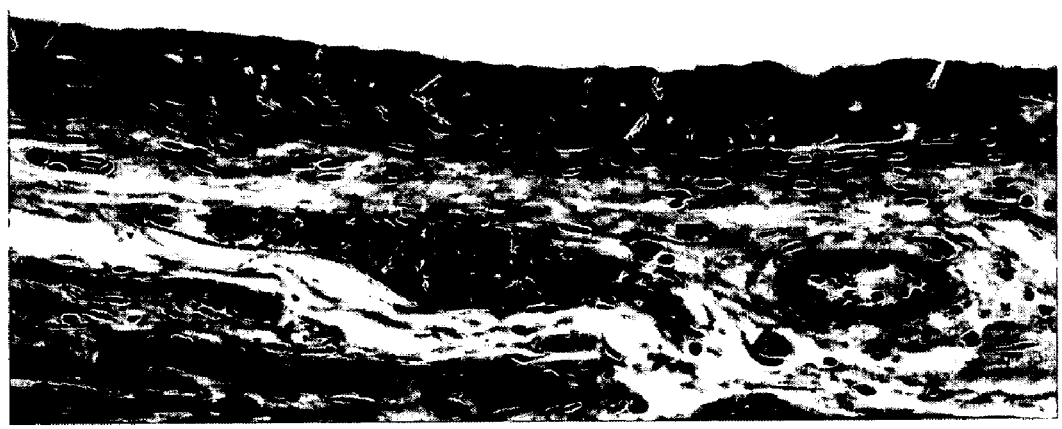
40x
FIG. 22C

100x

40x

40x

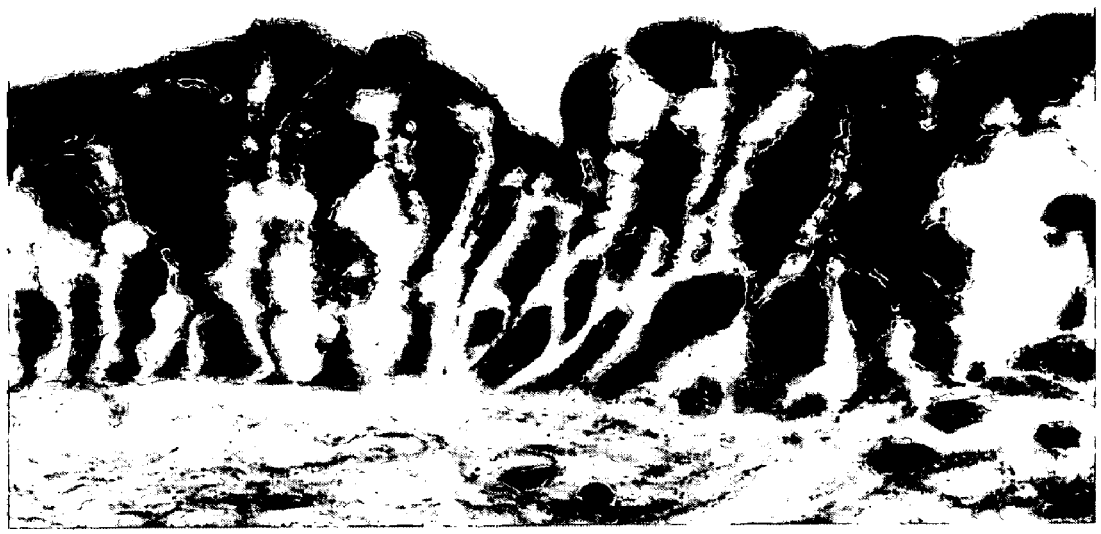
100x        FIG. 24C

40x

100x

100x

40x

100x

40x

40x

100x

100x

METHODS AND REAGENTS FOR THE ENHANCEMENT OF VIRUS TRANSDUCTION IN THE BLADDER EPITHELIUM

This application is a continuation-in-part of U.S. patent application Ser. No. 10/327,869, filed Dec. 26, 2002, which application is incorporated herein by reference in its entirety.

BACKGROUND OF THE INVENTION

1. Field of the Invention

The present invention relates generally to the treatment of bladder cancer with viral therapy agents and, in particular, to agents and methods for enhancing recombinant oncolytic virus transduction of the bladder epithelium.

2. Background of the Technology

Bladder cancer is a commonly occurring cancer and more than 50,000 new cases are diagnosed every year. Bladder cancer is a superficial disease confined to the mucosa in the majority of patients. Of the various therapeutic modalities available, transurethral resectioning of the tumor is considered to be the most effective treatment for the management of superficial bladder cancer. However, 70% of these superficial bladder tumors will recur after endoscopic resectioning, and 20% progress to life-threatening invasive diseases within 2 years of cystectomy. See Raghavan, et al., "Biology and Management of Bladder Cancer", N. Engl. J. Med., 322, 16, 1129-1138 (1990).

Gene therapy has also been used for the treatment of bladder cancer. See, for example, Brewster, et al., Eur. Urol. 25, 177-182 (1984); Takahashi, et al., Proc. Natl. Acad. Sci. USA 88, 5257-5261 (1991); and Rosenberg, J. Clin. Oncol., 10, 180-199 (1992).

In vitro studies using cell lines derived from human bladder tissues have demonstrated efficient transgene expression following infection with recombinant adenovirus. Bass, et al., Cancer Gene Therapy 2, 2, 97-104 (1995). Experiments in vivo have also shown adenovirus transgene expression in the urinary bladder of rodents after intravesical administration. Bass, et al., supra; Morris, et al., J. Urology, 152, 506-550 (1994). In vitro experiments with wild-type adenovirus demonstrate that virus attachment and internalization is not influenced by benzyl alcohol, but do demonstrate an enhanced uncoating of the virion. Blixt. et al., Arch. Virol., 129, 265-277 (1993).

In vivo studies have demonstrated that various agents (e.g. acetone, DMSO, protamine sulfate) can break down the protective "mucin" layer that protects the bladder epithelium from bacteria, viruses and other pathogens. See, for example, Monson, et al., J. Urol., 145, 842-845 (1992) and Parsons, et al., J. Urol., 143, 139-142 (1990). Methods of modifying the bladder surface to enhance gene transfer have also been disclosed. Siemens. et al., "Evaluation of Gene Transfer Efficiency by Viral Vectors to Murine Bladder Epithelium", J. of Urology, 165, 667-671 (2001).

U.S. Pat. No. 6,165,779 discloses a gene delivery system formulated in a buffer comprising a delivery-enhancing agent such as ethanol or a detergent. The gene delivery system may be a recombinant viral vector such as an adenoviral vector.

There still exists a need, however, for improved gene therapy methods and agents which can accomplish direct, optimal, in vivo gene delivery to the bladder epithelium.

SUMMARY OF THE INVENTION

According to a first aspect of the invention, a method for treating cancer of the bladder is provided. According to this aspect of the invention, the method involves: contacting the luminal surface of the bladder with a pretreatment composition comprising a transduction enhancing agent; and subsequently contacting the luminal surface of the bladder with a composition comprising an oncolytic virus; wherein the transduction enhancing agent is a mono-, di-, or polysaccharide having a lipophilic substituent. The transduction enhancing agent can have the following general formula (I) or the following general formula (II):

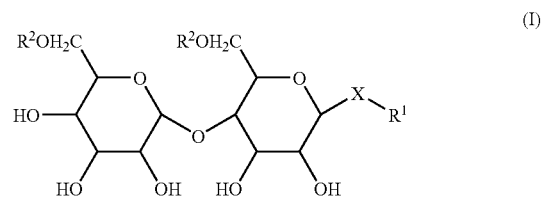

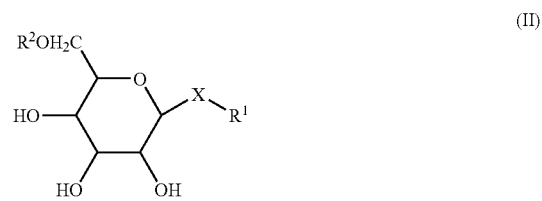

wherein X is a sulfur or oxygen atom, $R^1$ is an alkyl group and each $R^2$ is independently hydrogen or a moiety represented by:

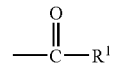

wherein $R^1$ is an alkyl group. The pretreatment composition can further include an oxidizing agent. The oncolytic virus can be an oncolytic adenovirus such as CG8840. The oncolytic virus composition can further include a chemotherapeutic agent such as docetaxel.

According to a second aspect of the invention, a method for treating cancer of the bladder is provided. According to this aspect of the invention, the method includes contacting the luminal surface of the bladder with a pretreatment composition comprising about 0.01 to about 0.2% by weight sodium oxychlorosene and, subsequently, contacting the luminal surface of the bladder with a composition comprising an oncolytic virus.

According to a third aspect of the invention, a method of treating cancer of the bladder is provided. According to this aspect of the invention, the method includes: contacting the luminal surface of the bladder with a pretreatment composition comprising a transduction enhancing agent having a structure represented by the chemical formula:

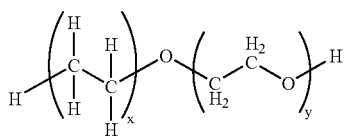

wherein x and y are positive integers; and subsequently contacting the luminal surface of the bladder with a composition comprising an oncolytic virus. According to a preferred embodiment of the invention, x is 6 and y is 8-10 and the pretreatment composition comprises about 0.02 to about 0.05 wt. % of the transduction enhancing agent.

According to a fourth aspect of the invention, a method of treating cancer of the bladder is provided. According to this aspect of the invention, the method includes: contacting the luminal surface of the bladder with a pretreatment composition comprising a transduction enhancing agent having a structure represented by the following general formula (I) or the following general formula (II):

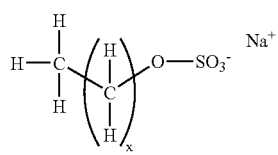

(I)

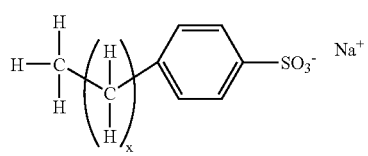

(II)

wherein x is a positive integer and subsequently contacting the luminal surface of the bladder with a composition comprising an oncolytic virus.

According to a fifth aspect of the invention, a composition comprising a transduction enhancing agent and an oncolytic virus is provided. According to this aspect of the invention, the transduction enhancing agent is a mono-, di-, or polysaccharide having a lipophilic substituent. For example, the transduction enhancing agent can be a compound having the following general formula (I) or the following general formula (II):

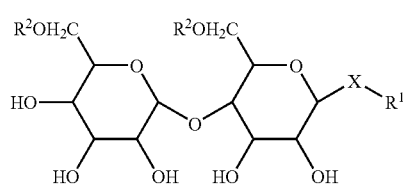

(I)

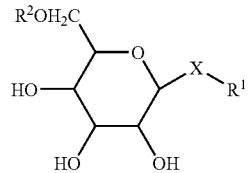

(II)

wherein X is a sulfur or oxygen atom, $R^1$ is an alkyl group and each $R^2$ is independently hydrogen or a moiety represented by:

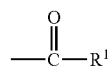

wherein $R^1$ is an alkyl group. The oncolytic virus can be an oncolytic adenovirus such as CG8840. The oncolytic virus composition can further include a chemotherapeutic agent such as docetaxel. A method for treating cancer of the bladder comprising contacting the luminal surface of the bladder with a composition as set forth above is also provided.

According to a sixth aspect of the invention, a composition comprising sodium oxychlorosene and an oncolytic virus is provided. The oncolytic virus can be an oncolytic adenovirus such as CG8840. The oncolytic virus composition can further include a chemotherapeutic agent such as docetaxel. A method for treating cancer of the bladder comprising contacting the luminal surface of the bladder with a composition as set forth above is also provided.

BRIEF DESCRIPTION OF THE DRAWINGS

The present invention may be better understood with reference to the accompanying drawings in which:

FIGS. 1A and 1B are photographs showing a murine bladder after pretreatment with a 15% ethanol solution followed by infection with Ad-LacZ wherein FIG. 1A shows the outside surface of the bladder and FIG. 1B shows the luminal bladder surface;

FIGS. 1C and 1D are photographs showing a murine bladder after pretreatment with a 20% ethanol solution followed by infection with Ad-LacZ wherein FIG. 1C shows the outside surface of the bladder and FIG. 1D shows the luminal bladder surface;

FIGS. 1E and 1F are photographs showing a murine bladder after pretreatment with a 25% ethanol solution followed by infection with Ad-LacZ wherein FIG. 1E shows the outside surface of the bladder and FIG. 1F shows the luminal bladder surface;

FIGS. 1G and 1H are photographs showing a murine bladder after pretreatment with a 30% ethanol solution followed by infection with Ad-LacZ wherein FIG. 1G shows the outside surface of the bladder and FIG. 1H shows the luminal bladder surface;

FIGS. 5A-5D are photographs showing two murine bladders after pretreatment with a 4% poloxomer 407 solution followed by infection with Ad-LacZ wherein FIGS. 5A and 5B show the outside and luminal surfaces, respectively, of the first bladder and FIGS. 5C and 5D show the outside and luminal surfaces, respectively, of the second bladder;

FIGS. 6A-6D are photographs showing two murine bladders after infection with a composition comprising lipofectamine and Ad-LacZ wherein FIGS. 6A and 6B show the outside and luminal surfaces, respectively, of the first bladder and FIGS. 6C and 6D show the outside and luminal surfaces, respectively, of the second bladder;

FIGS. 7A-7D are photographs showing two murine bladders after infection with a composition comprising In vivo geneSHUTTLE™ and Ad-LacZ wherein FIGS. 7A and 7B show the outside and luminal surfaces, respectively, of the first bladder and FIGS. 7C and 7D show the outside and luminal surfaces, respectively, of the second bladder;

FIGS. 8A-8N are photographs showing seven murine bladders after pretreatment with a 0.2% oxychlorosene solution for 5 minutes followed by infection with Ad-LacZ wherein FIGS. 8A and 8B show the outside and luminal surfaces, respectively, of the first bladder, FIGS. 8M and 8N show the outside and luminal surfaces, respectively, of the seventh bladder;

FIGS. 9A-9N are photographs showing seven murine bladders after pretreatment with a 0.2% oxychlorosene solution for 15 minutes followed by infection with Ad-LacZ wherein FIGS. 9A and 9B show the outside and luminal surfaces, respectively, of the first bladder, FIGS. 9M and 9N show the outside and luminal surfaces, respectively, of the seventh bladder;

FIG. 17A is a photograph showing the luminal surface of a first murine bladder after pretreatment with a 0.4% oxychlorosene solution followed by infection with Ad-LacZ;

FIGS. 17B and 17C are photographs showing the cross section of the murine bladder of FIG. 17A wherein FIG. 17B was taken at 40× and FIG. 17C was taken at 100× magnification;

FIG. 21A and 21B are photographs showing the outside and luminal surfaces, respectively, of a first murine bladder after pretreatment with a 0.05% polidocanol solution followed by infection with Ad-LacZ;

FIGS. 21C and 21D are photographs showing the cross section of the murine bladder of FIG. 21A wherein FIG. 21B was taken at 40× and FIG. 21C was taken at 100× magnification;

FIGS. 22A and 22B are photographs showing the outside and luminal surfaces, respectively, of a second murine bladder after pretreatment with a 0.05% polidocanol solution followed by infection with Ad-LacZ;

FIGS. 22C and 22D are photographs showing the cross section of the murine bladder of FIG. 22A wherein FIG. 22B was taken at 40× and FIG. 22C was taken at 100× magnification;

FIGS. 24B and 24C are photographs showing the cross section of the murine bladder of FIG. 24A wherein FIG. 24B was taken at 40× and FIG. 24C was taken at 100× magnification;

DETAILED DESCRIPTION OF THE PREFERRED EMBODIMENTS

Figure 1A:
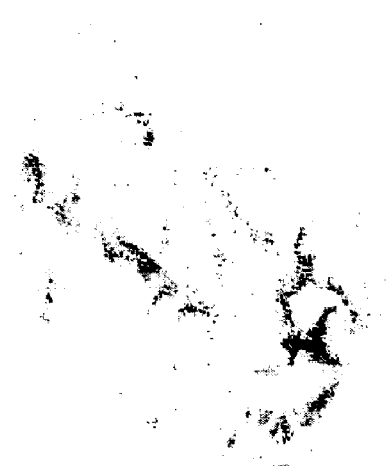

The present invention is directed to the use of transduction enhancing agents to render the bladder umbrella cell layer more susceptible to infection with a viral gene delivery vehicle than it would be without treatment. Exemplary transduction enhancing agents according to the invention include: dodecyl surfactants; dodecylmaltosides; dodecyl alcohol polyoxyethylene ethers (i.e., polidocanol); and sodium dodecylbenzenesulphonic acid/hypochlorous acid complex (i.e., oxychlorosene).

According to the invention, the luminal surface of the bladder can be treated with a composition comprising a transduction enhancing agent prior to infection with a viral gene delivery vehicle. The viral gene delivery vehicle can be an oncolytic virus used to treat bladder cancer. Oncolytic viruses for use in practicing the invention include, but are not limited to, adenovirus, herpes simplex virus (HSV), reovirus, vesicular stomatitis virus (VSV), newcastle disease virus, vacinia virus, influenza virus, West Nile virus, coxsackie virus, poliovirus and measles virus. Of particular interest in practicing the invention are oncolytic viruses that exhibit preferential expression in particular tissue types (i.e., in the bladder urothelium). An oncolytic adenovirus of this type is disclosed, for example, in Zhang, et al., "Identification of Human Uroplakin II Promoter and Its Use in the Construction of CG8840, a Urothelium-specific Adenovirus Variant that Eliminates Established Bladder Tumors in Combination with Docetaxel", Cancer Research, 62, 3743-3750 (2002) and in co-owned U.S. patent application Ser. No. 09/814,292, which is expressly incorporated by reference herein. Chemotherapeutic agents for use in combination therapy with oncolytic viruses are described, for example, in co-owned U.S. patent application Ser. No. 09/814,357, which is expressly incorporated by reference herein.

Alternatively, the viral gene delivery vehicle can be any gene therapy delivery vehicle known in the art for use in gene therapy, including, but not limited to, an adenovirus, an adeno-associated virus (AAV), a lentivirus, a retrovirus, a herpes virus, etc. Exemplary gene therapy adenoviral agents are disclosed in U.S. Pat. No. 6,165,779. The present inventors have found that pre-treating mouse bladders with aqueous solutions of various compounds consistently increased transduction to greater than 60% of the bladder surface, versus an untreated percent transduction of no more than 10%.

In addition to pre-treatment of the bladder surface with the transduction enhancing agent, the present invention includes co-administration of the viral gene delivery vehicle and the transduction enhancing agent to the bladder and to co-formulations of any one of the transduction enhancing agents with a recombinant viral gene delivery vehicle.

Composition and Chemistry of Reagents Used to Enhance Adenovirus Transduction in the Bladder Epithlelium Several classes of compounds, surfactants, and pre-made reagents were tested in order to find those which increased gene transfer or transduction by a viral gene delivery vehicle in the bladder. An oncolytic adenovirus, CG884, was used as an exemplary viral gene therapy vehicle. The reagents evaluated can be classified by their physical or chemical properties and structure.

First, the reagents can be grouped as a single compound or as a mixed reagent (i.e., a mixture of compounds). Single compounds evaluated include non-ionic surfactants, alcohols, polymers and ionic surfactants. The ionic surfactants evaluated included: 4% Poloxamer 407 (Pluronic® 127); 4% poloxamer 188 (Pluronic® F68); 0.02%-0.5% Polidocanol; 0.1% n-dodecyl-b-D-glucopyranoside (which can also be classified as a sugar-based surfactant); 0.02-0.5% n-dodecyl-b-D-maltoside (which can also be classified as a sugar-based surfactant); 0.1% Tween® 20; 0.1% Triton® X-100; 0.1% Forlan® C-24 (PEG Cholesterol); 0.1% decyl-b-D-maltoside (which can also be classified as a sugar-based surfactant); 0.1% 6-cyclohexylhexyl-β-D-maltoside (which can also be classified as a sugar-based surfactant); and 0.1% Tromboject® (sodium tetradecyl sulfate).

Alcohols evaluated include 0.1%-3% benzyl alcohol and 10%-30% ethanol. Polymers evaluated include 0.4% HPMC 2910; 0.4% PVA; 0.4% PVP; and 100 mg/ml Poly-Lysine. Ionic surfactants evaluated include: 0.1% DC-Chol [Cholesteryl 3b-N-(dimethylaminoethyl) carbamate]; 0.2% sodium salt of Dodecyl benzenesulfonic acid; and 0.1% sodium dodecyl sulfate. Mixed reagents evaluated include: In vivo GeneSHUTTLE™ (a reagent comprising DOTAP+ Cholesterol available from Qbiogene of Carlsbad, Calif.) and 0.1%-0.4% Oxychlorosene (sodium dodecylbenzenesulphonic acid/hypochlorous acid complex).

Effect of Ethanol Pretreatment on Adenovirus-Mediated Gene Transfer and Expression in The Bladder Epithelium of Rodents A study was conducted to evaluate the effect of ethanol pretreatment on adenovirus-mediated gene transfer and expression in the bladder epithelium of rodents.

Test Materials

Ad-βgal virus was made as a frozen formulation using standard conditions known in the art for freezing and formulation of adenovirus. The vehicle for the virus arm was PBS plus 10% glycerol. Pretreatment agents were 5%, 10%, 15%, 20% and 30% GLP grade ethanol, respectively, in PBS-10% glycerol solution.

Animals 80 female BALB/c mice were used for this study. Female animals are chosen because of the ease of urethral cannulation and vesicle instillation. The mice were approximately 10 to 12 weeks on the day of the start of the experiment.

Treatment Regimen

Animals were assigned to each group as shown in the following table.

TABLE 1

Effect of Ethanol pretreatment

| Group No. | Animals per group | Test Article | Route | Ethanol pre-treatment | Virus dose (particles/animal) | Dose Regimen |
|---|---|---|---|---|---|---|
| 1 | 8-10 | Vehicle | Intravesical | — | — | 100 ml PBS-10% glycerol on Day 1 |
| 2 | 8-10 | Ad-βgal | Intravesical | — | $1.3 \times 10^{11}$ | Ad-βgal on Day 1 |
| 3 | 8-10 | Ad-βgal | Intravesical | 5% ethanol | $1.3 \times 10^{11}$ | 5% ethanol pretreatment followed by virus administration on Day 1 |
| 4 | 8-10 | Ad-βgal | Intravesical | 10% ethanol | $1.3 \times 10^{11}$ | 10% ethanol pretreatment followed by virus administration on Day 1 |
| 5 | 8-10 | Ad-βgal | Intravesical | 15% ethanol | $1.3 \times 10^{11}$ | 15% ethanol pretreatment followed by virus administration on Day 1 |
| 6 | 8-10 | Ad-βgal | Intravesical | 20% ethanol | $1.3 \times 10^{11}$ | 20% ethanol pretreatment followed by virus administration on Day 1 |
| 7 | 8-10 | Ad-βgal | Intravesical | 25% ethanol | $1.3 \times 10^{11}$ | 25% ethanol pretreatment followed by virus administration on Day 1 |

TABLE 1-continued

Effect of Ethanol pretreatment

| Group No. | Animals per group | Test Article | Route | Ethanol pre-treatment | Virus dose (particles/ animal) | Dose Regimen |
|---|---|---|---|---|---|---|
| 8 | 8-10 | Ad-βgal | Intravesical | 30% ethanol | $1.3 \times 10^{11}$ | 30% ethanol pretreatment followed by virus administration on Day 1 |

For the data in Table 1, the concentration of Ad-βgal virus was $1.3 \times 10^{12}$ vp/ml as determined by optical density measurements.

Treatment Procedure

1. Animals were anesthetized with isoflurane and a 24 g catheter introduced through the urethra into the bladder.

2. Residual urine was emptied and the bladder was flushed 3 times with 100-150 µl each of PBS.

3. In test animals, bladders were pretreated for 20 minutes with 0.1 ml of 5, 10, 15, 20, 25 or 30% ethanol solution, respectively, and then rinsed 3 times with 100-150 µl of PBS.

4. Ad-βgal viruses diluted in 0.1 ml of PBS-10% glycerol were administered intravesically into the bladder and retained in the bladder for 45 minutes. A knot was placed around the urethral orifice to prevent leakage of the virus and to prevent the catheter from dislodging.

5. Treatment was stopped by withdrawing the virus and flushing the bladders 3 times with 100-150 µl of PBS. If the catheter became clogged, the washing step was avoided so that the virus was flushed out in the urine. However, the use of this procedure may prevent determination of the viral resident time in the bladder.

Measurement/Determinations

The clinical condition of the animals was observed before dosing on the day of treatment and the animals were observed daily during the experimental period.

Assessment of β-Galactosidase Activity

Animals were killed 48 hours after treatment. Bladders were filled with 0.1 ml whole organ fixative: 2% Neutral buffered formalin, 2% glutaraldehyde, 2 mM $MgCl_2$, 10 mM PBS, pH 7.4. Bladders were then removed and immersed in whole organ fixative for 1 hr. Thereafter, the bladders were cut open longitudinally, rinsed (2 mM $MgCl_2$, 0.1% deoxycholate, 0.2% Triton) for 24 hours at 4° C., and submerged into X-gal staining solution. Transgene expression in the luminal epithelium of the longitudinally opened bladders was empirically determined.

Histopathology

Bladders fixed in whole organ fixative were sectioned and stained with hematoxylin-eosin for histologic examination.

Results

Figure 1B:
Figure 1C:
Figure 1D:
Figure 1E:
Figure 1F:
Figure 1G:
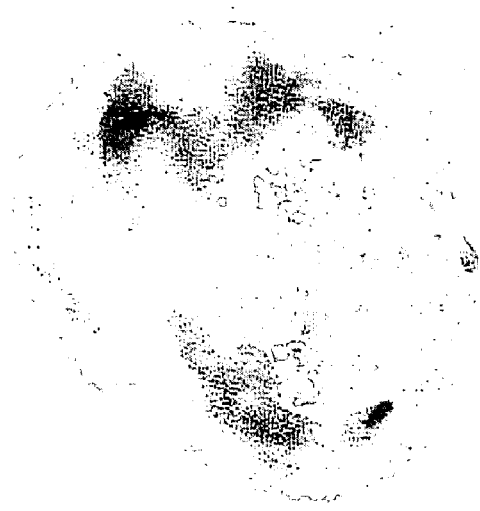
Figure 1H:

Pretreatment of the luminal bladder surface with various concentrations of ethanol (i.e., 15%, 20%, 25%, and 30 wt-%) for 20 minutes resulted in 10-20% transduction. FIGS. 1-4 show transduction of murine bladders after pretreatment with ethanol. FIGS. 1A and 1B are photographs showing a murine bladder after pretreatment with a 15% ethanol solution followed by infection with Ad-LacZ. FIG. 1A shows the outside surface of the bladder and FIG. 1B shows the luminal bladder surface. FIGS. 1C and 1D are photographs showing a murine bladder after pretreatment with a 20% ethanol solution followed by infection with Ad-LacZ. FIG. 1C shows the outside surface of the bladder and FIG. 1D shows the luminal bladder surface. FIGS. 1E and 1F are photographs showing a murine bladder after pretreatment with a 25% ethanol solution followed by infection with Ad-LacZ. FIG. 1E shows the outside surface of the bladder and FIG. 1F shows the luminal bladder surface. FIGS. 1G and 1H are photographs showing a murine bladder after pretreatment with a 30% ethanol solution followed by infection with Ad-LacZ. FIG. 1G shows the outside surface of the bladder and FIG. 1H shows the luminal bladder surface. As can be seen from FIG. 1, higher concentrations of ethanol resulted in greater levels of transduction as measured by staining.

Figure 2A:
FIG. 2A ia a photograph showing a cross section of a murine bladder control.
Figure 2B:
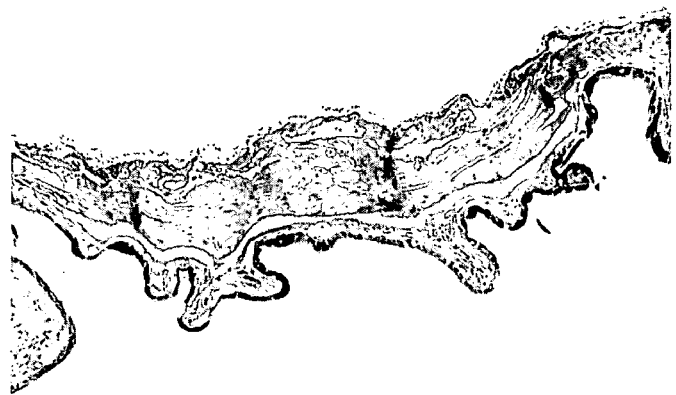
FIGS. 2B and 2C are photographs showing the cross section of a murine bladder after pretreatment with a 30% ethanol solution followed by infection with Ad-LacZ.
Figure 2C:
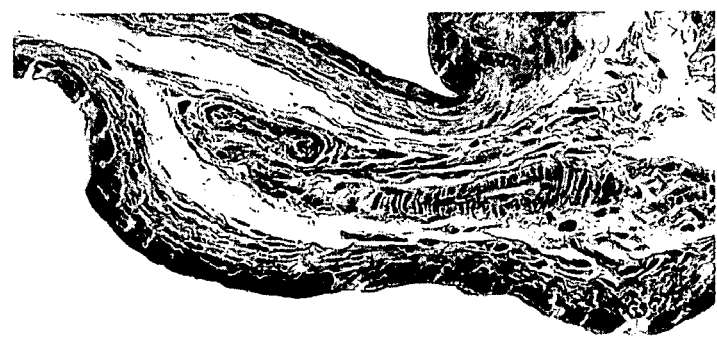

FIG. 2A is a photograph showing a cross section of a murine bladder control (i.e., no pretreatment). FIGS. 2B and 2C are photographs showing the cross section of a murine bladder after pretreatment with a 30% ethanol solution followed by infection with Ad-LacZ.

Figure 3A:
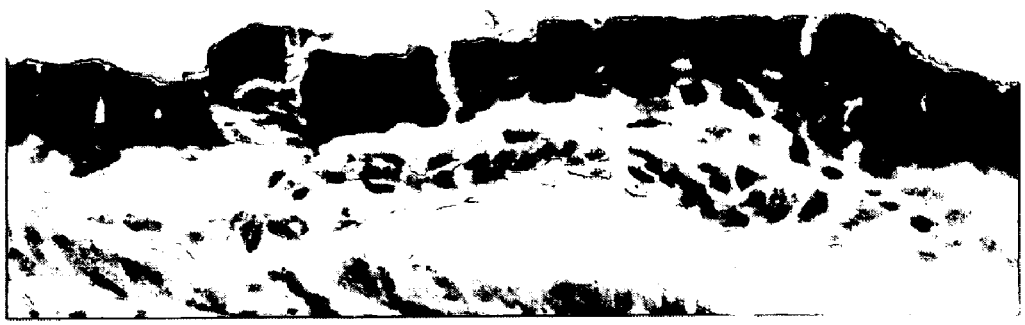
FIGS. 3A-3F are photographs showing the cross section of a murine bladder after pretreatment with a 25% ethanol solution followed by infection with Ad-LacZ wherein FIGS. 3A, 3C and 3E were taken at 40× and FIGS. 3B, 3D and 3F were taken at 100× magnification.
Figure 3B:
Figure 3C:
Figure 3D:
Figure 3E:
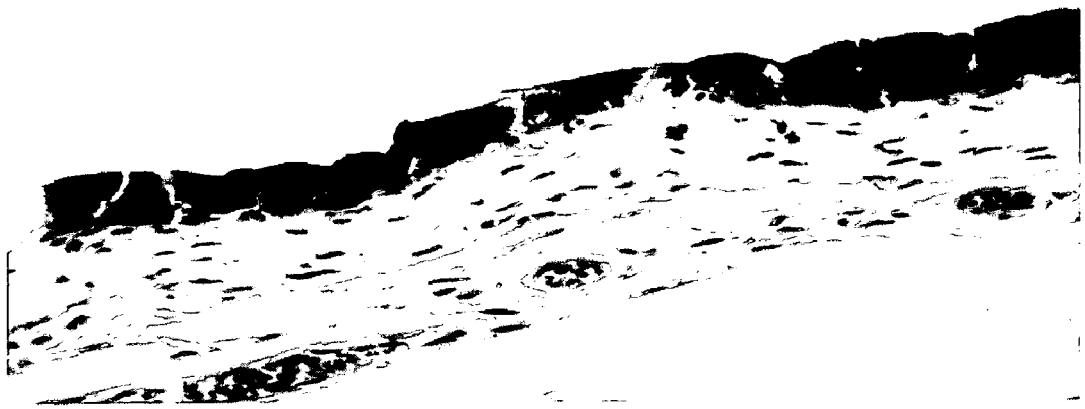
Figure 3F:

FIGS. 3A-3F are photographs showing the cross section of three murine bladders after pretreatment with a 25% ethanol solution followed by infection with Ad-LacZ. FIGS. 3A and 3B are photographs showing the cross-section of the first murine bladder, FIGS. 3C and 3D are photographs showing the cross-section of the second murine bladder, and FIGS. 3E and 3F are photographs showing the cross-section of the third murine bladder. FIGS. 3A, 3C and 3E were taken at 40× and FIGS. 3B, 3D and 3F were taken at 100× magnification.

Figure 4A:
FIGS. 4A-4F are photographs showing the cross section of a murine bladder after pretreatment with a 30% ethanol solution followed by infection with Ad-LacZ wherein FIGS. 4A, 4C and 4E were taken at 40× and FIGS. 4B, 4D and 4F were taken at 100× magnification.
Figure 4B:
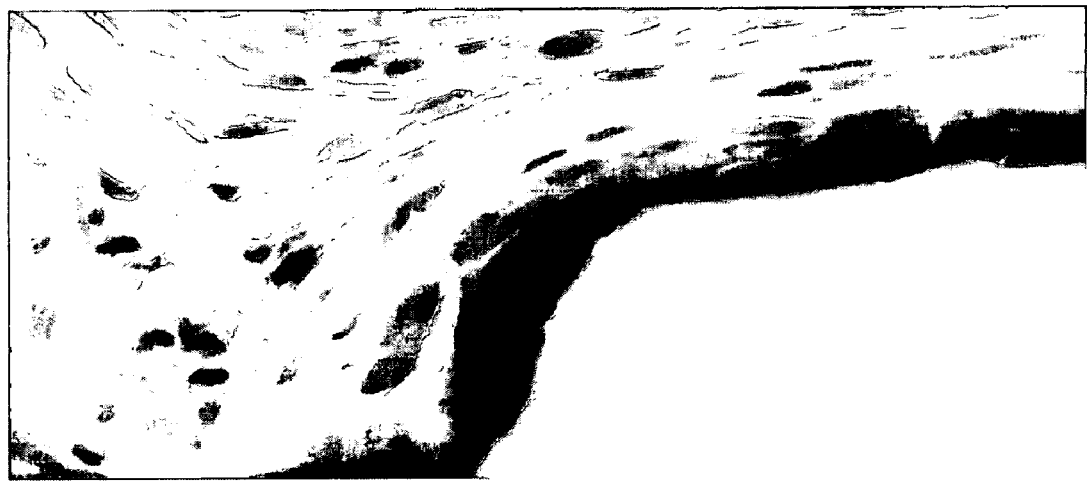
Figure 4C:
Figure 4D:
Figure 4E:
Figure 4F:
Figure 6A:
Figure 6B:
Figure 6C:
Figure 6D:

FIGS. 4A-4F are photographs showing the cross section of three murine bladders after pretreatment with a 30% ethanol solution followed by infection with Ad-LacZ. FIGS. 4A and 4B are photographs showing the cross-section of the first murine bladder, FIGS. 4C and 4D are photographs showing the cross-section of the second murine bladder, and FIGS. 4E and 4F are photographs showing the cross-section of the third murine bladder. FIGS. 4A, 4C and 4E were taken at 40× and FIGS. 4B, 4D and 4F were taken at 100× magnification.

Effect of Chemical Agent Pretreatment on Adenovirus-Mediated Gene Transfer and Expression in the Bladder Epithelium of Rodent A study was conducted to evaluate the effect of chemical agent pretreatment on adenovirus-mediated gene transfer and expression in the bladder epithelium of rodents.

Test Materials

Ad-βgal virus was made at CGI, as a frozen formulation using standard conditions known in the art for freezing and formulation of adenovirus. The vehicle for the virus arm was PBS plus 10% glycerol.

Animals 152 female BALB/c mice were used this study. Female animals were chosen because of the ease of urethral cannulation and vesicle instillation. The mice were approximately 10 to 12 weeks on the day of the start of the experiment.

Treatment Regimen

Animals were assigned to each group shown in the following table. The route of administration of the chemical agent and virus was intravesical.

TABLE 2

Effect of Chemical Agent Pretreatment

| Group No. | Animals per group | Test Article | Chemical agent | Virus dose (particles/ animal) | Dose Regimen |
|---|---|---|---|---|---|
| 1 | 2 | Vehicle | 4% Poloxamer 407 (Pluronic 127) | — | 100 ml of 4% Poloxamer 407 (Pluronic 127) in PBS-10% glycerol on Day 1 |
| 2 | 6-8 | Ad-βgal | 4% Poloxamer 407 (Pluronic 127) | $1.3 \times 10^{11}$ | 4% Poloxomer 407 (Pluronic 127) pretreatment followed by virus administration on Day 1 |
| 3 | 2 | Vehicle | 4% Poloxamer 188 (Pluronic F68) | | 100 ml of 4% Poloxamer 188 (Plluronic F68) in PBS-10% glycerol on Day 1 |
| 1 | 2 | Vehicle | 4% Poloxamer 407 (Pluronic 127) | — | 100 ml of 4% Poloxamer 407 (Pluronic 127) in PBS-10% glycerol on Day 1 |
| 4 | 6-8 | Ad-βgal | 4% Poloxamer 188 (Pluronic F68) | $1.3 \times 10^{11}$ | 4% Poloxomer 188 (Pluronic F68) pretreatment following by virus administration on Day 1 |
| 5 | 2 | Vehicle | Lipofectamine 2000 | | 100 ml of Lipofectamine 2000 (20 mg/ml) in PBS 10% glycerol. |
| 6 | 6-8 | Ad-βgal | Lipofectamine 2000 | $0.65 \times 10^{11}$ | 1.25 mg of Lipofectamine 2000 mixed with virus administration on Day 1 |
| 7 | 2 | Vehicle | 3% Benzyl Alcohol | | 100 μl of 3% Benzyl Alcohol in PBS-10% glycerol on Day 1 |
| 8 | 6-8 | Ad-βgal | 3% Benzyl Alcohol | $1 \times 10^{11}$ | 3% Benzyl Alcohol pretreatment followed by virus administration on Day 1 |
| 9 | 2 | Vehicle | 0.2% Oxychlorosene | | 0.2% Oxychlorosene in PBS-10% glycerol on Day 1 |
| 10 | 6-8 | Ad-βgal | 0.2% Oxychlorosene | $1.3 \times 10^{11}$ | 0.2% Oxychlorosene pretreatment (only wash) followed by virus administration on Day 1 |
| 11 | 6-8 | Ad-βgal | 0.2% Oxychlorosene | $1.3 \times 10^{11}$ | 0.2% Oxychlorosene pretreatment (5 min) followed by virus administration on Day 1 |
| 12 | 6-8 | Ad-βgal | 0.2% Oxychlorosene | $1.3 \times 10^{11}$ | 0.2% Oxychlorosene pretreatment (15 min) followed by virus administration on Day 1 |
| 13 | 2 | Vehicle | 0.05% Polidocanol | | 0.05% Polidocanol in PBS-10% glycerol on Day 1 |

TABLE 2-continued

Effect of Chemical Agent Pretreatment

| Group No. | Animals per group | Test Article | Chemical agent | Virus dose (particles/animal) | Dose Regimen |
|---|---|---|---|---|---|
| 1 | 2 | Vehicle | 4% Poloxamer 407 (Pluronic 127) | — | 100 ml of 4% Poloxamer 407 (Pluronic 127) in PBS-10% glycerol on Day 1 |
| 14 | 6-8 | Ad-βgal | 0.05% Polidocanol | $1.3 \times 10^{11}$ | 0.05% Polidocanol pretreatment followed by virus administration on Day 1 |
| 15 | 2 | Vehicle | 0.1% DC-Chol | | 0.1% DC-Chol in PBS-10% glycerol on Day 1 |
| 16 | 6-8 | Ad-βgal | 0.1% DC-Chol | $1.3 \times 10^{11}$ | 0.1% DC-Chol pretreatment followed by virus administration on Day 1 |
| 17 | 2 | Vehicle | In vivo Gene Shuttle (DOTAP + Cholesterol) | | 4 mM solution in PBS |
| 18 | 6-8 | Ad-βgal | In vivo Gene Shuttle (DOTAP + Cholesterol) | $0.65 \times 10^{11}$ | 4 mM of In vivo Gene Shuttle mixed with virus. Administration on Day 1. (Dilute 60 ml of Lipid with 90 ml of water. Then add 150 ul of Ad-bgal) |
| 19 | 2 | Vehicle | 0.5% Polidocanol | | 0.5% Polidocanol in PBS-10% glycerol on Day 1 |
| 20 | 6-8 | Ad-βgal | 0.5% Polidocanol | $1.3 \times 10^{11}$ | 0.5% Polidocanol pretreatment followed by virus administration on Day 1 |
| 21 | 2 | Vehicle | 0.4% HPMC 2910 | | 0.4% HPMC 2910 in PBS-10% glycerol on Day 1 |
| 22 | 6-8 | Ad-βgal | 0.4% HPMC 2910 | $0.5 \times 10^{11}$ | 0.8% HPMC 2910 mixed with an equal volume of the virus and then administered on Day 1 |
| 23 | 2 | Vehicle | 100 mg/ml Poly-Lysine | | 100 ug/ml Poly-Lysine in PBS-10% glycerol on Day 1 |
| 1 | 2 | Vehicle | 4% Poloxamer 407 (Pluronic 127) | — | 100 ml of 4% Poloxamer 407 (Pluronic 127) in PBS-10% glycerol on Day 1 |
| 24 | 6-8 | Ad-βgal | 100 mg/ml Poly-Lysine | $0.5 \times 10^{11}$ | 200 ug/ml Poly-Lysine mixed with an equal volume of the virus and then administered on Day 1 |
| 25 | 2 | Vehicle | 0.1% n-dodecyl-b-D glucopyranoside | | 0.1% n-dodecyl-b-D glucopyranoside in PBS-10% glycerol on Day 1 |
| 26 | 6-8 | Ad-βgal | 0.1% n-dodecyl-b-D glucopyranoside | $1 \times 10^{11}$ | 0.1% n-dodecyl-b-D glucopyranoside pretreatment followed by virus administration on Day 1 |
| 27 | 2 | Vehicle | 0.4% PVA | | 0.4% PVA in PBS-10% glycerol on Day 1 |
| 28 | 6-8 | Ad-βgal | 0.4% PVA | $0.5 \times 10^{11}$ | 0.8% PVA mixed with an equal volume of the virus and then administered on Day 1 |
| 29 | 2 | Vehicle | 0.4% PVP | | 0.4% PVP in PBS-10% glycerol on Day 1 |
| 30 | 6-8 | Ad-βgal | 0.4% PVP | $0.5 \times 10^{11}$ | 0.8% PVP mixed with an equal volume of the virus and then administered on Day 1 |

TABLE 2-continued

Effect of Chemical Agent Pretreatment

| Group No. | Animals per group | Test Article | Chemical agent | Virus dose (particles/ animal) | Dose Regimen |
|---|---|---|---|---|---|
| 31 | 2 | Vehicle | 0.1% Cholesterol-Cyclodextrin reagent | | 0.1% Cholesterol-Cyclodextrin reagent in PBS-10% glycerol on Day 1 |
| 32 | 6-8 | Ad-βgal | 0.1% Cholesterol-Cyclodextrin reagent | $0.5 \times 10^{11}$ | 0.2% Cholesterol-Cyclodextrin reagent mixed with an equal volume of the virus and then administered on Day 1 |
| 33 | 2 | Vehicle | 0.05% n-Dodecyl b-D-Maltoside | | 0.05% n-Dodecyl b-D-Maltoside in PBS-10% glycerol on Day 1 |
| 1 | 2 | Vehicle | 4% Poloxamer 407 (Pluronic 127) | — | 100 ml of 4% Poloxamer 407 (Pluronic 127) in PBS-10% glycerol on Day 1 |
| 34 | 6-8 | Ad-βgal | 0.05% n-Dodecyl b-D-Maltoside | $1 \times 10^{11}$ | 0.05% n-Dodecyl b-D-Maltoside pretreatment followed by virus administration on Day 1 |
| 35 | 2 | Vehicle | 0.3% Benzyl Alcohol | | 100 μl of 0.3% Benzyl Alcohol in PBS-10% glycerol on Day 1 |
| 36 | 6-8 | Ad-βgal | 0.3% Benzyl Alcohol | $1 \times 10^{11}$ | 0.3% Benzyl Alcohol pretreatment followed by virus administration on Day 1 |
| 37 | 2 | Vehicle | 0.1% Benzyl Alcohol | | 100 μl of 0.1% Benzyl Alcohol in PBS-10% glycerol on Day 1 |
| 38 | 6-8 | Ad-βgal | 0.1% Benzyl Alcohol | $1 \times 10^{11}$ | 0.1% Benzyl Alcohol pretreatment followed by virus administration on Day 1 |
| 39 | 2 | Vehicle | 0.1% Oxychlorosene | | 0.1% Oxychlorosene in PBS-10% glycerol on Day 1 |
| 40 | 6-8 | Ad-βgal | 0.1% Oxychlorosene | $1 \times 10^{11}$ | 0.1% Oxychlorosene pretreatment (5 min) followed by virus administration on Day 1 |
| 41 | 2 | Vehicle | 0.4% Oxychlorosene | | 0.4% Oxychlorosene in PBS-10% glycerol on Day 1 |
| 42 | 6-8 | Ad-βgal | 0.4% Oxychlorosene | $1 \times 10^{11}$ | 0.4% Oxychlorosene pretreatment (5 min) followed by virus administration on Day 1 |
| 43 | 2 | Vehicle | 0.02% Polidocanol | | 0.02% Polidocanol in PBS-10% glycerol on Day 1 |
| 1 | 2 | Vehicle | 4% Poloxamer 407 (Pluronic 127) | — | 100 ml of 4% Poloxamer 407 (Pluronic 127) in PBS-10% glycerol on Day 1 |
| 44 | 6-8 | Ad-βgal | 0.02% Polidocanol | $1 \times 10^{11}$ | 0.02% Polidocanol pretreatment followed by virus administration on Day 1 |
| 45 | 2 | Vehicle | 0.2% Polidocanol | | 0.2% Polidocanol in PBS-10% glycerol on Day 1 |
| 46 | 6-8 | Ad-βgal | 0.2% Polidocanol | $1 \times 10^{11}$ | 0.2% Polidocanol pretreatment followed by virus administration on Day 1 |

TABLE 2-continued

Effect of Chemical Agent Pretreatment

| Group No. | Animals per group | Test Article | Chemical agent | Virus dose (particles/ animal) | Dose Regimen |
|---|---|---|---|---|---|
| 47 | 2 | Vehicle | 0.02% n-Dodecyl b-D-Maltoside | | 0.02% n-Dodecyl b-D-Maltoside in PBS-10% glycerol on Day 1 |
| 48 | 6-8 | Ad-βgal | 0.02% n-Dodecyl b-D-Maltoside | $1 \times 10^{11}$ | 0.02% n-Dodecyl b-D-Maltoside pretreatment followed by virus administration on Day 1 |
| 49 | 2 | Vehicle | 0.2% n-Dodecyl b-D-Maltoside | | 0.2% n-Dodecyl b-D-Maltoside in PBS-10% glycerol on Day 1 |
| 50 | 6-8 | Ad-βgal | 0.2% n-Dodecyl b-D-Maltoside | $1 \times 10^{11}$ | 0.2% n-Dodecyl b-D-Maltoside pretreatment followed by virus administration on Day 1 |
| 51 | 2 | Vehicle | 0.2% sodium salt of Dodecyl benzenesulfonic acid | | 0.2% sodium salt of Dodecyl benzenesulfonic acid in PBS-10% glycerol on Day 1 |
| 52 | 6-8 | Ad-βgal | 0.2% sodium salt of Dodecyl benzenesulfonic acid | $1 \times 10^{11}$ | 0.2% sodium salt of Dodecyl benzenesulfonic acid pretreatment followed by virus administration on Day 1 |
| 1 | 2 | Vehicle | 4% Poloxamer 407 (Pluronic 127) | — | 100 ml of 4% Poloxamer 407 (Pluronic 127) in PBS-10% glycerol on Day 1 |
| 53 | 2 | Vehicle | 0.1% sodium dodecyl sulphate | | 0.1% sodium dodecyl sulphate in PBS-10% glycerol on Day 1 |
| 54 | 6-8 | Ad-βgal | 0.1% sodium dodecyl sulphate | $1 \times 10^{11}$ | 0.1% sodium dodecyl sulphate pretreatment followed by virus administration on Day 1 |
| 55 | 2 | Vehicle | 0.1% Tween 20 | | 0.1% Tween 20 in PBS-10% glycerol on Day 1 |
| 56 | 6-8 | Ad-βgal | 0.1% Tween 20 | $1 \times 10^{11}$ | 0.1% Tween 20 pretreatment followed by virus administration on Day 1 |
| 57 | 2 | Vehicle | 0.1% Triton X-100 | | 0.1% Triton X-100 in PBS-10% glycerol on Day 1 |
| 58 | 6-8 | Ad-βgal | 0.1% Triton X-100 | $1 \times 10^{11}$ | 0.1% Triton X-100 pretreatment followed by virus administration on Day 1 |
| 59 | 2 | Vehicle | 0.1% Forlan C-24 (PEG Cholesterol) | | 0.1% Forlan C-24 in PBS-10% glycerol on Day 1 |
| 60 | 6-8 | Ad-βgal | 0.1% Forlan C-24 (PEG Cholesterol) | $1 \times 10^{11}$ | 0.1% Forlan C-24 pretreatment followed by virus administration on Day 1 |
| 61 | 2 | Vehicle | 0.1% Decyl-b-D-Maltoside | | 0.1% Decyl-b-D-Maltoside in PBS-10% glycerol on Day 1 |
| 62 | 6-8 | Ad-βgal | 0.1% Decyl-b-D-Maltoside | $1 \times 10^{11}$ | 0.1% Decyl-b-D-Maltoside pretreatment followed by virus administration on Day 1 |

TABLE 2-continued

Effect of Chemical Agent Pretreatment

| Group No. | Animals per group | Test Article | Chemical agent | Virus dose (particles/ animal) | Dose Regimen |
|---|---|---|---|---|---|
| 63 | 2 | Vehicle | 0.1% 6-Cyclohexylhexyl-b-D-Maltoside | — | 0.1% 6-Cyclohexylhexyl-b-D-Maltoside in PBS-10% glycerol on Day 1 |
| 1 | 2 | Vehicle | 4% Poloxamer 407 (Pluronic 127) | — | 100 ml of 4% Poloxamer 407 (Pluronic 127) in PBS-10% glycerol on Day 1 |
| 64 | 6-8 | Ad-βgal | 0.1% 6-Cyclohexylhexyl-b-D-Maltoside | $1 \times 10^{11}$ | 0.1% 6-Cyclohexylhexyl-b-D-Maltoside pretreatment followed by virus administration on Day 1 |
| 65 | 2 | Vehicle | 0.1% Tromboject (Sodium Tetradecyl Sulfate) | — | 0.1% Tromboject in PBS-10% glycerol on Day 1 |
| 66 | 6-8 | Ad-βgal | 0.1% Tromboject (Sodium Tetradecyl Sulfate) | $1 \times 10^{11}$ | 0.1% Tromboject pretreatment followed by virus administration on Day 1 |
| 67 | 2 | Vehicle | 0.1% Phenyl B-D-Glucopyranoside | — | 0.1% Phenyl B-D-Glucopyranoside in PBS-10% glycerol on Day 1 |
| 68 | 6-8 | Ad-βgal | 0.1% Phenyl B-D-Glucopyranoside | $1 \times 10^{11}$ | 0.1% Phenyl B-D-Glucopyranoside pretreatment followed by virus administration on Day 1 |
| 69 | 2 | Vehicle | 0.1% Sucrose Monolaurate | — | 0.1% Sucrose Monolaurate in PBS-10% glycerol on Day 1 |
| 70 | 6-8 | Ad-βgal | 0.1% Sucrose Monolaurate | $1 \times 10^{11}$ | 0.1% Sucrose Monolaurate pretreatment followed by virus administration on Day 1 |
| 71 | 2 | Vehicle | 0.1% 1-O-dodecyl-rac-glycerol | — | 0.1% 1-O-dodecyl-rac-glycerol in PBS-10% glycerol on Day 1 |
| 72 | 6-8 | Ad-βgal | 0.1% 1-O-dodecyl-rac-glycerol | $1 \times 10^{11}$ | 0.1% 1-O-dodecyl-rac-glycerol pretreatment followed by virus administration on Day 1 |

The concentration of Ad-βgal virus for the data in Table 2 was $1.3 \times 10^{12}$ vp/ml (1st preparation, particle: PFU: 30) and $1 \times 10^{12}$ vp/ml (2nd preparation, particle: PFU: 30) as determined by optical density measurements.

Treatment Procedure

1. The animals were anesthetized with isoflurane and a 24 g catheter was introduced through the urethra into the bladder.

2. Residual urine was emptied and the bladder was flushed 3 times with 100 μl each of PBS.

3. Based on the reagent being tested, bladder pretreatment was performed as follows:

Poloxomer 407 procedure: Washed 2 times with 100 μl each. Retained the $3^{rd}$ wash for 5 min and gave one additional wash. Performed 3 times PBS wash prior to virus instillation.

Poloxomer 188 procedure: Washed 2 times with 100 μl each. Retained the $3^{rd}$ wash for 5 minutes and gave one additional wash. Performed 3 times PBS wash prior to virus instillation.

Lipofectamine 2000 procedure: Added 5 μl of stock Lipofectamine (1 mg/ml) to 195 μl of PBS-10% glycerol. Mixed with an equal volume of Ad-βgal virus and incubated for 15 minutes. Administered 100 μl of the mixture intravesically and retained in the bladder for 30 minutes.

Benzyl Alcohol procedure: Washed 2 times with 100 μl each. Retained the $3^{rd}$ wash for 15 minutes and then gave one additional wash. Performed 3 times PBS wash prior to virus instillation.

Oxychlorosene procedure: Washing performed as mentioned in the dose regimen (i.e., 3 washes of 100 μl each, one wash but retained for 5 min., one wash but retained for 15 min). Performed 3 times PBS wash prior to virus instillation.

Polidocanol procedure: Washed 2 times with 100 μl each. Retained the $3^{rd}$ wash for 5 min and then gave one additional wash. Performed 3 times PBS wash prior to virus instillation.

DC-Cho procedure: Washed 2 times with 100 µl each. Retained the 3rd wash for 5 min and then gave one additional wash. Performed 3 times PBS wash prior to virus instillation.

0.4% HPMC 2910 procedure: No pretreatment. An equal volume of the virus was mixed with 0.8% solution of HPMC2910 and the mixture was instilled into the bladder for 30 minutes.

100 mg/ml Poly-Lysine procedure: No pretreatment. An equal volume of the virus was mixed with 100 mg/ml solution of Poly-Lysine and the mixture was instilled into the bladder for 30 minutes.

0.4% polyvinyl alcohol (PVA) procedure: No pretreatment. An equal volume of the virus was mixed with 0.8% solution of PVA and the mixture was instilled into the bladder for 30 minutes.

n-dodecyl-β-D glucopyranoside procedure: Washed 2 times with 100 µl each. Retained the 3rd wash for 5 min and then gave one additional wash. Performed 3 times PBS wash prior to virus instillation.

0.4% PVP procedure: No pretreatment. An equal volume of the virus was mixed with 0.8% solution of PVP and the mixture was instilled into the bladder for 30 min.

0.1% cholesterol-cyclodextrin reagent procedure: No pretreatment. An equal volume of the virus was mixed with 0.2% solution of Cholesterol-Cyclodextrin and the mixture was instilled into the bladder for 30 minutes.

n-dodecyl-β-D-maltoside procedure: Washed 2 times with 100 µl each. Retained the 3rd wash for 5 min and then gave one additional wash. Performed 3 times PBS wash prior to virus instillation.

Sodium salt of dodecyl benzenesulfonic acid procedure: Washed 2 times with 100 µl each. Retained the 3rd wash for 5 min and then gave one additional wash. Performed 3 times PBS wash prior to virus instillation.

0.1%سcroll sodium dodecyl sulphate procedure: Wash 2 times with 100 µl each. Retained the 3rd wash for 5 min and then gave one additional wash. Performed 3 times PBS wash prior to virus instillation.

0.1% Tween 20 procedure: Washed 2 times with 100 µl each. Retained the 3rd wash for 5 min and then gave one additional wash. Performed 3 times PBS wash prior to virus instillation.

0.1% Triton® X-100 procedure: Washed 2 times with 100 µl each. Retained the 3rd wash for 5 min and then gave one additional wash. Perform 3 times PBS wash prior to virus instillation.

0.1% Forlan C-24 procedure: Washed 2 times with 100 µl each. Retained the 3rd wash for 5 min and then gave one additional wash. Performed 3 times PBS wash prior to virus instillation.

0.1% decyl-b-D-maltoside procedure: Washed 2 times with 100 µl each. Retained the 3rd wash for 5 min and then gave one additional wash. Performed 3 times PBS wash prior to virus instillation.

0.1% 6-cyclohexylhexyl-b-D-maltoside procedure: Washed 2 times with 100 µl each. Retained the 3rd wash for 5 min and then gave one additional wash. Performed 3 times PBS wash prior to virus instillation.

0.1% sodium tetradecyl sulfate (Tromboject®, Omega Laboratories Ltd.) procedure: Washed 2 times with 100 µl each. Retained the 3rd wash for 5 min and then gave one additional wash. Performed 3 times PBS wash prior to virus instillation.

0.1% phenyl-β-D-glucopyranoside procedure: Washed 2 times with 100 µl each. Retained the 3rd wash for 5 min and then gave one additional wash. Performed 3 times PBS wash prior to virus instillation.

0.1% sucrose monolaurate procedure: Washed 2 times with 100 µl each. Retained the 3rd wash for 5 min and then gave one additional wash. Performed 3 times PBS wash prior to virus instillation.

0.1% 1-O-dodecyl-rac-glycerol procedure: Washed 2 times with 100 µl each. Retained the 3rd wash for 5 min and then gave one additional wash. Performed 3 times PBS wash prior to virus instillation.

In vivo geneSHUTTLE™ procedure. Mixed 4 mM of In vivo geneSHUTTLE™ with virus. Administration on Day 1. Diluted 60 ml of Lipid with 90 ml of water. Then added 150 µl of Ad-βgal.

4. Virus treatment (45 min) stopped by withdrawing the virus and flushing the bladders 3 times with 100 µl of PBS.

Measurement/Determinations

The clinical condition of the animals were observed before dosing on the day of treatment, and animals were observed daily during the experimental period.

Assessment of β-Galactosidase Activity

Animals were killed 48 hours after treatment. The bladders were filled with 0.1-ml whole organ fixative: 2% Neutral buffered formalin, 2% glutaraldehyde, 2 mM $MgCl_2$, 10 mM PBS, pH 7.4. The bladders were then removed and immersed in whole organ fixative for 1 hour. Thereafter, each bladder was cut open longitudinally, rinsed (in 2 mM $MgCl_2$, 0.1% deoxycholate, 0.2% Triton) for 24 hours at 4° C., and submerged into X-gal staining solution. Transgene expression in the luminal epithelium of the longitudinally opened bladders was empirically determined.

Histopathology

Bladders fixed in whole organ fixative were sectioned and stained with hematoxylin-eosin for histologic examination.

Results

The results of the above experiments can be summarized as follows:

Pre-treatment of the bladder with 4% Poloxamer 407 (Pluronic 127) for 5 minutes resulted in <5% transduction.

Treatment of the bladder with a lipofectamine and virus mixture (no pretreatment) resulted in <5% transduction.

Treatment of the bladder with an In vivo geneSHUTTLE™ and virus mix (no bladder pretreatment) resulted in <5% transduction.

A pre-treatment of the bladder with 0.1% oxychlorosene for 5 minutes resulted in >90% transduction of the urothelium. The pathologists report indicated mild submucosal edema with intact epithelial layer.

A pre-treatment of the bladder with 0.2% oxychlorosene for 5 minutes resulted in >90% transduction of the urothelium. The pathologists report indicated minimal submucosal edema and perivascular lymphocytes.

A pre-treatment of the bladder with 0.2% oxychlorosene for 15 minutes resulted in >90% transduction of Urothelium. The pathologists report indicated focal severe ulceration with suppurtative exudate, hemorrhage and edema in the submucosa.

A pre-treatment of the bladder with 0.4% oxychlorosene for 5 minutes resulted in >90% transduction of Urothelium. The pathologists report indicated moderate submucosal edema with focal large ulcer.

A pre-treatment of the bladder with 0.02% polidocanol for 5 minutes resulted in 10-20% transduction of the urothelium. The pathologists report indicated an intact mucosa.

A pre-treatment of the bladder with 0.05% polidocanol for 5 minutes resulted in 30-40% transduction of the urothelium. The pathologists report indicated minimal submucosal edema.

A pre-treatment of the bladder with 0.2% polidocanol for 5 minutes resulted in 50-80% transduction of Urothelium. The pathologists report indicated erosions and focal ulcer as well as mucosal compromise.

A pre-treatment of the bladder with 0.02% n-dodecyl β-D-maltoside for 5 minutes resulted in 50-80% transduction of the urothelium. The pathologists report indicated no significant lesions.

A pre-treatment of the bladder with 0.05% n-dodecyl β-D-maltoside for 5 minutes resulted in >90% transduction of the urothelium. The pathologists report indicated no significant lesions.

A pre-treatment of the bladder with 0.2% n-dodecyl β-D-maltoside for 5 minutes resulted in >90% transduction of the urothelium. The pathologists report indicated erosions, focal ulcer, moderate submucosal edema with mucosal compromise.

A pre-treatment of the bladder with 0.2% dodecyl benzenesulfonic acid for 5 minutes resulted in 20-40% transduction of the urothelium.

As can be seen from the above results, several single compounds and one mixed reagent showed significantly increased transduction as measured by the levels of final blue stain (LacZ). Several other single compounds resulted in enhanced but smaller levels of transduction. An ethanol pre-treatment was used as a reference to validate each chemical tested. Even with an ethanol percentage as high as 30%, only 10-20% transduction was observed. The "strong responders" were those transduction enhancing agents which exhibited significantly better (i.e., 70-90% staining) than the ethanol pre-treatment controls, which exhibited 10-20% staining. The weak responders had significantly less stained area compared to the ethanol control group.

The strongest response (i.e., highest level of transduction) was observed following pretreatment of the bladder surface with: 0.02%-0.5% polidocanol; 0.02-0.5% n-dodecyl-b-D-maltoside; 0.1% 6-cyclohexylhexyl-b-D-maltoside; 0.1%-0.4% oxychlorosene; 0.2% sodium salt of dodecyl benzenesulfonic acid; and 0.1% sodium dodecyl sulphate.

The "weak responders" included 0.1% decyl-b-D-maltoside and 0.1% Triton® X-100.

Although not wishing to be bound by theory, the mechanism of action can be hypothesized by analyzing the physical and chemical properties of successful transduction enhancing reagents. The transduction enhancing reagent in general is a surfactant. The surfactant can be ionic or non-ionic. The surfactant preferably has both hydrophilic and lipophilic sections. The hydrophilic portion of the molecule contributes to water solubility while the lipophilic (i.e., hydrophobic) portion helps molecular interactions with lipids. The hydrophilic/lipophilic balance or HLB ratio is an indication of the relative size of each part of the molecule.

Sugar Based Surfactants (Saccharides)

The transduction enhancing agent according to the invention can be a sugar (e.g., a mono-, di-, or poly-saccharide) having a lipophilic substituent. The transduction enhancing agent can be any mono-, di-, or poly-saccharide having a lipophilic substituent. According to a preferred embodiment of the invention, the transduction enhancing agent is a di-saccharide having a lipophilic substituent. Exemplary di-saccharides include maltose or sucrose. Other di-saccharides having lipophilic substituents, however, can also be used including lactose, isomaltose, trehalose or cellobiose.

The lipophilic substituent can be linear (e.g., a straight chain n-alkane or alkene) or non-linear (e.g., cyclic or branched chain alkanes or alkenes). The lipophilic substituent can also be an alkanoic acid residue. The length of the lipophilic substituent can be varied to achieve the desired hydrophilic-lipophilic balance. Tests on various maltoside substituted compounds indicated that a sufficient lipophilic length resulted in improved transduction efficacy. For example, both n-dodecyl-β-D-maltoside and 6-cyclohexyl-hexyl-β-D-maltoside increased transduction significantly. In contrast, n-decyl-β-D-maltoside had only a slight effect on transduction.

Results for bladder pretreatment with n-dodecyl-β-D-maltoside are shown in FIGS. 25-29. FIG. 25A is a photograph showing the luminal surface of a first murine bladder after pretreatment with a 0.02% n-dodecyl β-D-maltoside solution followed by infection with Ad-LacZ. FIGS. 25B and 25C are photographs showing the cross section of the murine bladder of FIG. 25A. FIG. 25B was taken at 40× and FIG. 25C was taken at 100× magnification. FIG. 26A is a photograph showing the luminal surface of a second murine bladder after pretreatment with a 0.02% n-dodecyl β-D-maltoside solution followed by infection with Ad-LacZ. FIGS. 26B and 26C are photographs showing the cross section of the murine bladder of FIG. 26A. FIG. 26B was taken at 40× and FIG. 26C was taken at 100× magnification. FIG. 27A is a photograph showing the luminal surface of a first murine bladder after pretreatment with a 0.05% n-dodecyl β-D-maltoside solution followed by infection with Ad-LacZ. FIGS. 27B and 27C are photographs showing the cross section of the murine bladder of FIG. 27A. FIG. 27B was taken at 40× and FIG. 27C was taken at 100× magnification. FIG. 28A is a photograph showing the luminal surface of a first murine bladder after pretreatment with a 0.05% n-dodecyl β-D-maltoside solution followed by infection with Ad-LacZ. FIGS. 28B and 28C are photographs showing the cross section of the murine bladder of FIG. 28A. FIG. 28B was taken at 40× and FIG. 28C was taken at 100× magnification. FIG. 29A is a photograph showing the luminal surface of a first murine bladder after pretreatment with a 0.2% n-dodecyl β-D-maltoside solution followed by infection with Ad-LacZ. FIGS. 29B and 29C are photographs showing the cross section of the murine bladder of FIG. 29A. FIG. 29B was taken at 40× and FIG. 29C was taken at 100× magnification.

The chemical formula for n-dodecyl-β-D-maltoside and n-decyl-β-D-maltoside is given below:

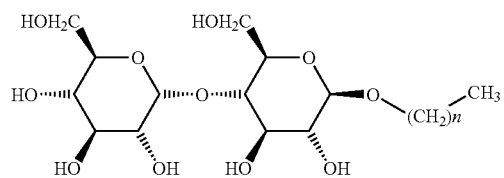

where n is 11 and 9, respectively. The chemical formula for 6-cyclohexylhexyl-β-D-maltoside is:

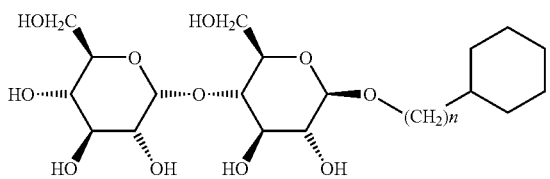

where n is 6.

The transduction experiments demonstrated that a small reduction in the size of the lipophilic side chain (i.e., CH$_2$—CH$_2$) can limit the efficacy of the molecule for transduction enhancement to a great degree. It is important to note that all of the above compounds had good solubility in both water and PBS buffer.

Compounds in this class of surfactants having a shorter hydrophilic moiety were also evaluated. The results for n-dodecyl-β-D-glucopyranoside showed little or no enhancement of transduction. The chemical formula for n-dodecyl-β-D-glucopyranoside is:

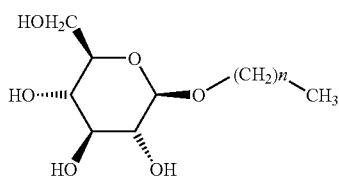

where n is 11. While not wishing to be bound by theory, the relative sizes of the hydrophilic and lipophilic portions of the molecule appear to influence transduction enhancement. Therefore, shorter chain n-alkyl-β-D-glucopyranosides (e.g., n-hexyl-β-D-glucopyranoside) may exhibit improved transduction.

Any mono-, di-, or poly-saccharide having a lipophilic substituent can be used as a transduction enhancing agent according to the invention. Exemplary di-saccharide compounds include sucrose, lactose, maltose, isomaltose, trehalose, and cellobiose. The lipophilic substituent preferably comprises an alkyl or alkenyl group. According to a preferred embodiment of the invention, the lipophilic substituent is an alkanoic acid residue.

Although the β-forms of the mono- and di-saccharides are described above, the α-forms of these and other mono-, di-, or poly-saccharide compounds can also be used according to the invention. Exemplary α-saccharide transduction enhancing agents according to the invention include n-dodecyl-α-D-maltoside, n-hexyl-α-D-glucopyranoside and 6-cyclohexylhexyl-α-D-maltoside. Additionally, either the D- or L forms of the mono-, di-, or poly-saccharides may be used as transduction enhancing agents according to the invention.

Figure 31A:
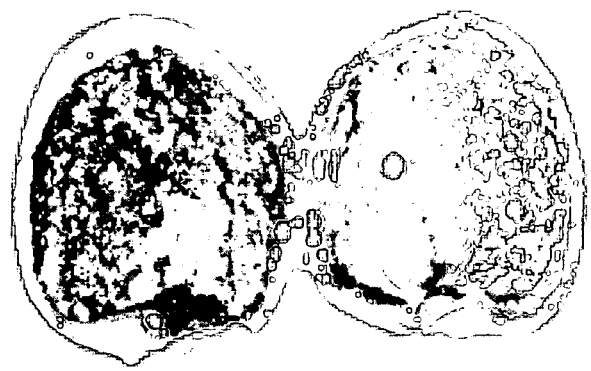
FIGS. 31A-31E are photographs showing the luminal surfaces of murine bladders treated with alkyl maltoside and alkyl maltopyranoside pretreating agents having various length alkyl side chains.
Figure 31B:
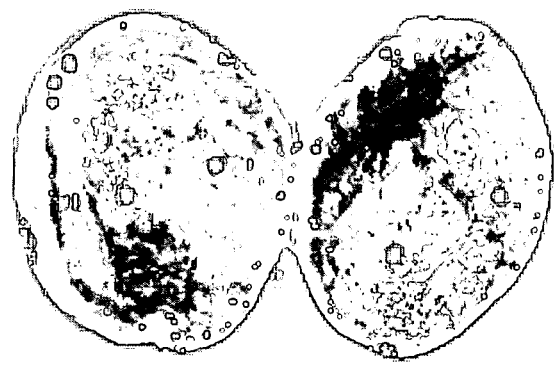
Figure 31C:

FIGS. 31A-31E are photographs showing the luminal surfaces of murine bladders treated with alkyl maltoside and alkyl maltopyranoside pretreating agents having various length alkyl side chains. FIG. 31A is a photograph of the luminal surface of a murine bladder treated with n-dodecyl-β-D-maltoside (C12 alkyl side chain) prior to infection with Ad-LacZ (10$^9$ vp). FIG. 31B shows the luminal surface of a murine bladder treated with tridecyl-β-D-maltopyranoside (C13 alkyl side chain) prior to infection. FIG. 31C shows the luminal surface of a murine bladder treated with n-tetradecyl-β-D-maltoside (C14 alkyl side chain) prior to infection.

Figure 31D:
Figure 31E:

FIG. 31D shows the luminal surface of a murine bladder treated with n-decyl-β-D-maltoside (C10 alkyl side chain) prior to infection. FIG. 31E shows the luminal surface of a murine bladder treated with n-octyl-β-D-maltopyranoside (C8 alkyl side chain) prior to infection.

Ionic Alkyl Surfactants

Ionic alkyl surfactants can also be used as a transduction enhancing compounds according to the invention. Exemplary ionic alkyl surfactants include sodium dodecyl sulfate which has a formula represented by:

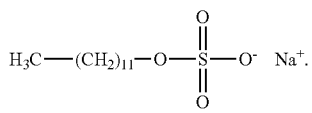

Another exemplary ionic surfactant is the sodium salt of dodecyl-benzenesulfonic acid which has a chemical formula represented by:

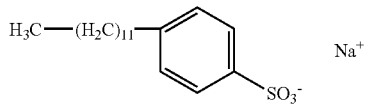

Figure 30A:
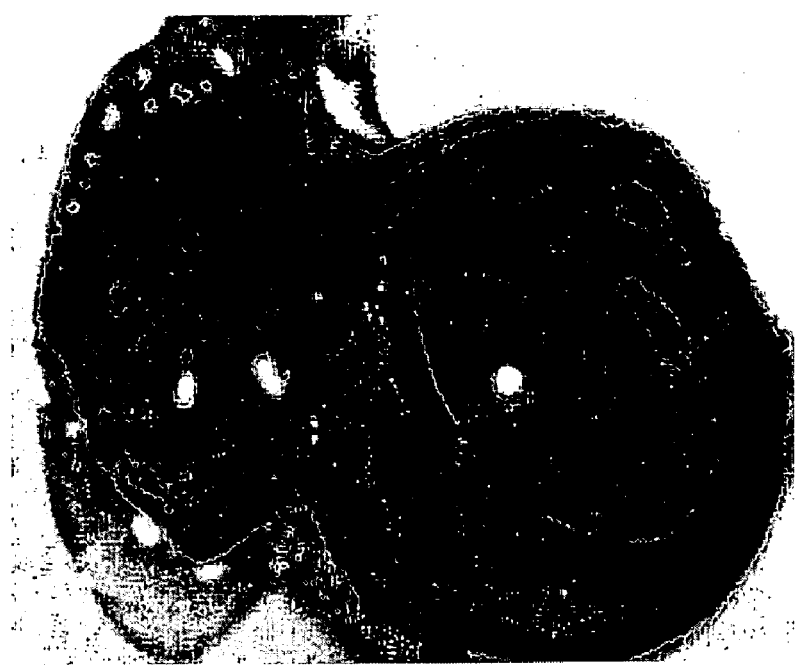
FIG. 30A is a photograph showing the luminal surface of a first murine bladder after pretreatment with a 0.2% sodium salt of dedecyl benzenesulfonic acid solution followed by infection with Ad-LacZ.
Figure 30B:
FIGS. 30B and 30C are photographs showing the cross section of the murine bladder of FIG. 30A wherein FIG. 30B was taken at 40× and FIG. 30C was taken at 100× magnification.
Figure 30C:

Surfactants of the above type were evaluated and were found to exhibit enhanced transduction comparable to the non-ionic reagents set forth above. These results are shown in FIG. 30 for dodecyl benzenesulfonic acid sodium salt. As can be seen by FIGS. 30A-30C, dodecyl benzenesulfonic acid sodium salt, enhanced the transduction of Ad-LacZ in murine bladders. FIG. 30A is a photograph showing the luminal surface of a first murine bladder after pretreatment with a 0.2% sodium salt of dedecyl benzenesulfonic acid solution followed by infection with Ad-LacZ. FIGS. 30B and 30C are photographs showing the cross section of the murine bladder of FIG. 30A. FIG. 30B was taken at 40× and FIG. 30C was taken at 100× magnification.

Figure 32A:
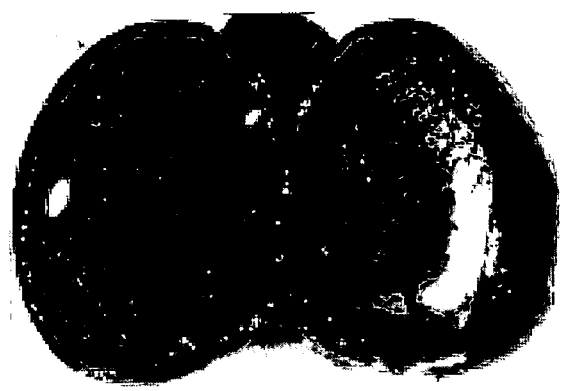
FIGS. 32A-32C are photographs showing the luminal surfaces of murine bladders treated with sodium alkyl sulfate pretreating agents having various length alkyl chains.
Figure 32B:
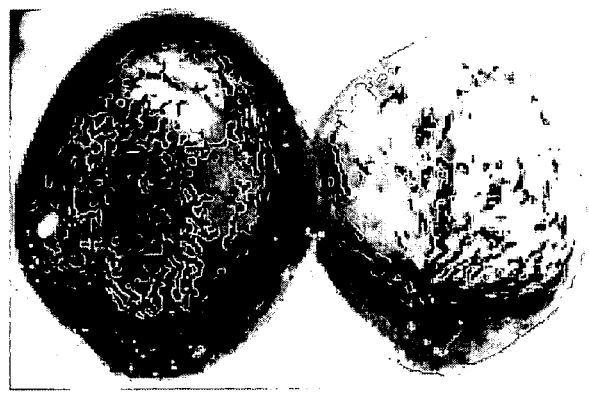
Figure 32C:
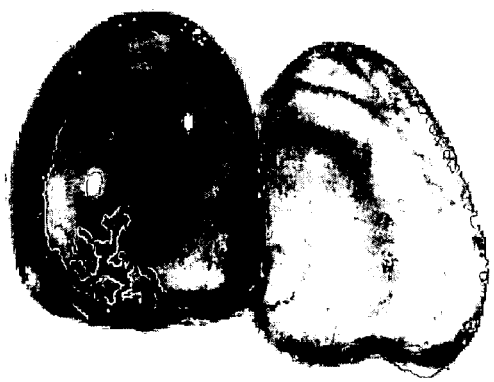

FIGS. 32A-32C are photographs showing the luminal surfaces of murine bladders treated with sodium alkyl sulfate pretreating agents having various length alkyl chains. FIG. 32A shows the luminal surface of a bladder treated with sodium dodecyl sulfate (SDS) (C12 alkyl side chain) prior to infection with Ad-LacZ (10$^9$ vp). FIG. 32B shows the luminal surface of a bladder treated with sodium decyl sulfate (C10 alkyl side chain) prior to infection. FIG. 32C shows the luminal surface of a bladder treated with sodium octyl sulfate (C8 alkyl side chain) prior to infection.

The ionic alkyl surfactants consist of two portions, a hydrophilic portion and a lipophilic portion. The arrangement of these portions of the molecule is similar to the sugar-based enhancing agents described above. According to the invention, compounds similar to those set forth above and having variations in alkyl substitution can also be used.

Alkyl(Ether) Alcohols

Also according to the invention, an alkyl ether compound can be used as a transduction enhancing compound. Polidocanol, an alkyl ether having the following chemical formula:

and a total formula of ~$C_{30}H_{62}O_{10}$, was evaluated. The polidocanol used in the evaluation was sold under the name Thesit®, which is a registered trademark of Desitin-Werk, Carl Klinke GmbH, Hamburg, Germany). There are several other chemical names for polidocanol such as polyethyleneglycoldodecyl ether [9002-92-0], lauryl alcohol, and macrogol lauryl ether.

Figure 19A:
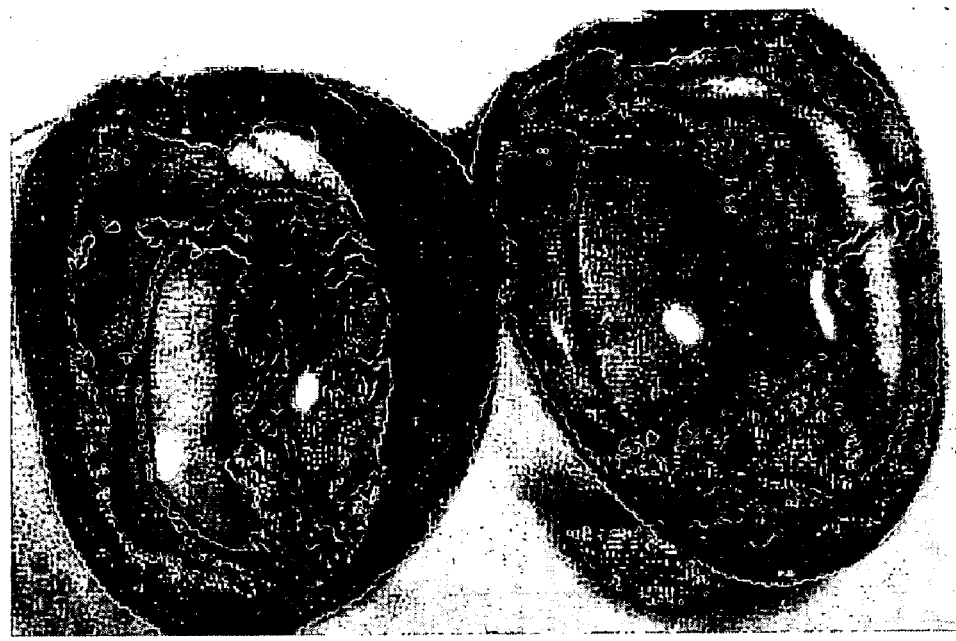
FIG. 19A is a photograph showing the luminal surface of a first murine bladder after pretreatment with a 0.02% polidocanol solution followed by infection with Ad-LacZ.
Figure 19B:
FIGS. 19B and 19C are photographs showing the cross section of the murine bladder of FIG. 19A wherein FIG. 19B was taken at 40× and FIG. 19C was taken at 100× magnification.
Figure 19C:
Figure 20A:
FIG. 20A is a photograph showing the luminal surface of a second murine bladder after pretreatment with a 0.02% polidocanol solution followed by infection with Ad-LacZ.
Figure 20B:
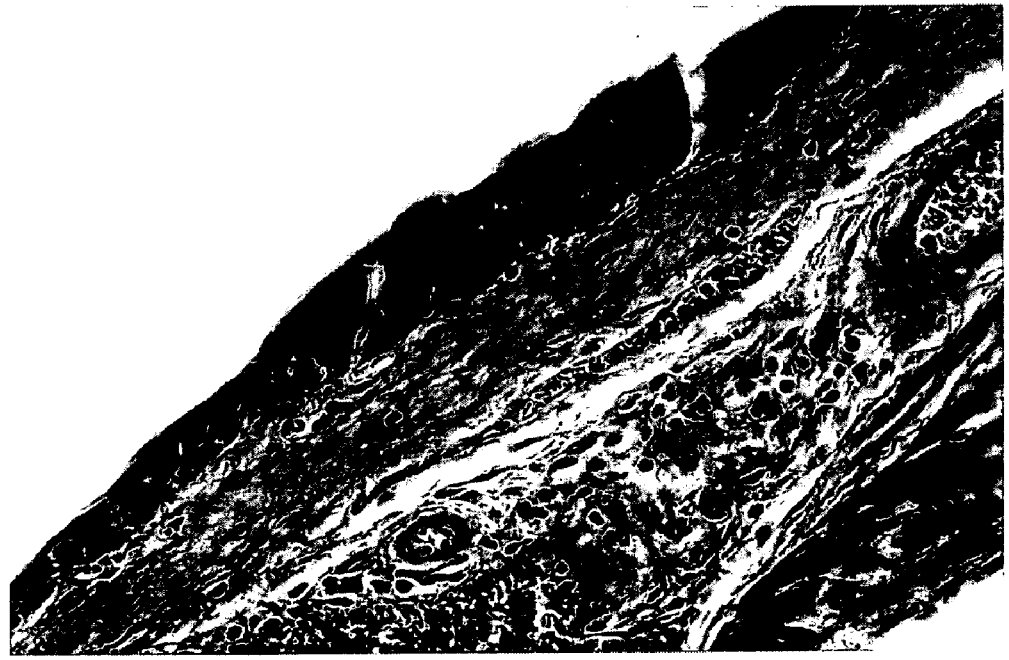
FIGS. 20B and 20C are photographs showing the cross section of the murine bladder of FIG. 20A wherein FIG. 20B was taken at 40× and FIG. 20C was taken at 100× magnification.
Figure 20C:

Results for pretreatment of the bladder surface with various concentrations of polidocanol are shown in FIGS. 19-24. Results for pretreatment of the bladder surface with 0.02% polidocanol are shown in FIGS. 19 and 20. FIG. 19A is a photograph showing the luminal surface of a first murine bladder after pretreatment with a 0.02% polidocanol solution followed by infection with Ad-LacZ. FIGS. 19B and 19C are photographs showing the cross section of the murine bladder of FIG. 19A. FIG. 19B was taken at 40× and FIG. 19C was taken at 100× magnification. FIG. 20A is a photograph showing the luminal surface of a second murine bladder after pretreatment with a 0.02% polidocanol solution followed by infection with Ad-LacZ. FIGS. 20B and 20C are photographs showing the cross section of the murine bladder of FIG. 20A. FIG. 20B was taken at 40× and FIG. 20C was taken at 100× magnification.

Figure 21D:
Figure 22D:

Results for pretreatment of the bladder surface with 0.05% polidocanol are shown in FIGS. 21 and 22. FIGS. 21A and 21B are photographs showing the outside and luminal surfaces, respectively, of a first murine bladder after pretreatment with a 0.05% polidocanol solution followed by infection with Ad-LacZ. FIGS. 21C and 21D are photographs showing the cross section of the murine bladder of FIG. 21A. FIG. 21B was taken at 40× and FIG. 21C was taken at 100× magnification. FIGS. 22A and 22B are photographs showing the outside and luminal surfaces, respectively, of a second murine bladder after pretreatment with a 0.05% polidocanol solution followed by infection with Ad-LacZ. FIGS. 22C and 22D are photographs showing the cross section of the murine bladder of FIG. 22A. FIG. 22B was taken at 40× and FIG. 22C was taken at 100× magnification.

Figure 23A:
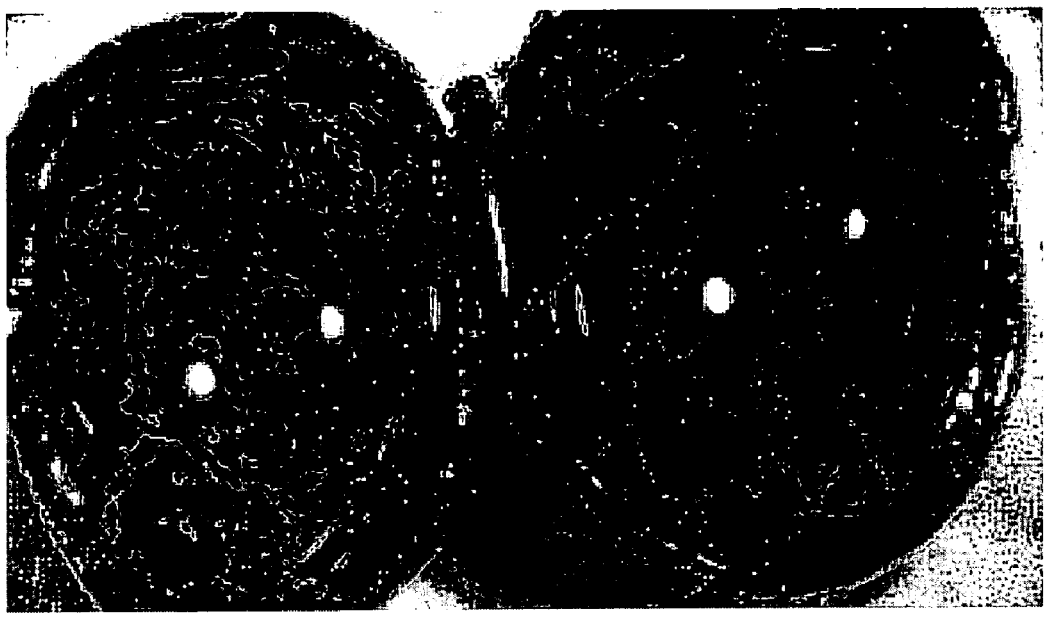
FIG. 23A is a photograph showing the luminal surface of a first murine bladder after pretreatment with a 0.2% polidocanol solution followed by infection with Ad-LacZ.
Figure 23B:
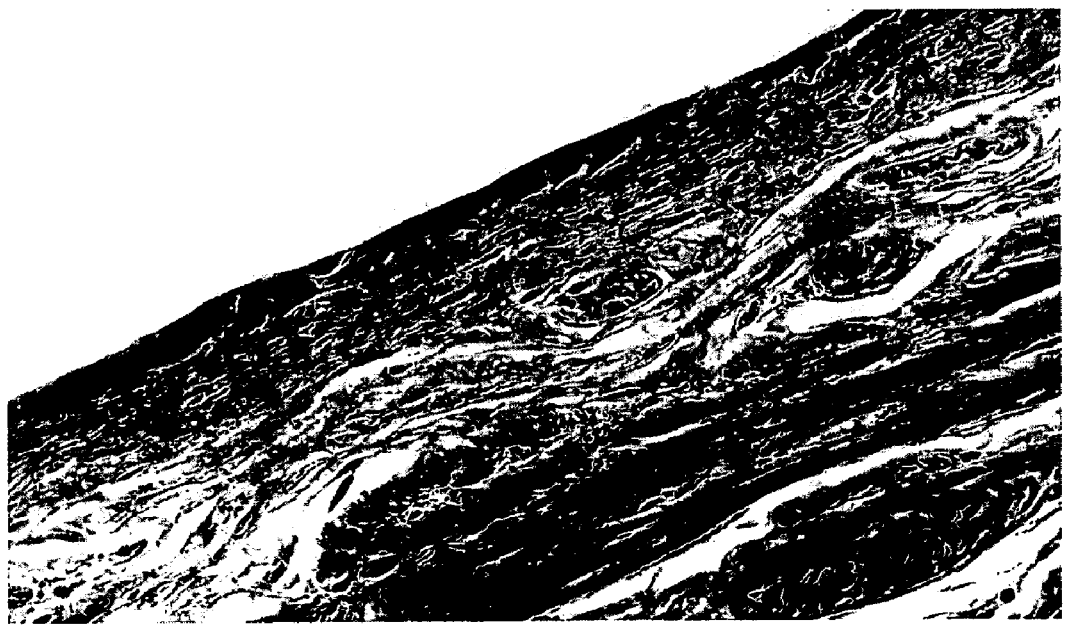
FIGS. 23B and 23C are photographs showing the cross section of the murine bladder of FIG. 23A wherein FIG. 23B was taken at 40× and FIG. 23C was taken at 100× magnification.
Figure 23C:
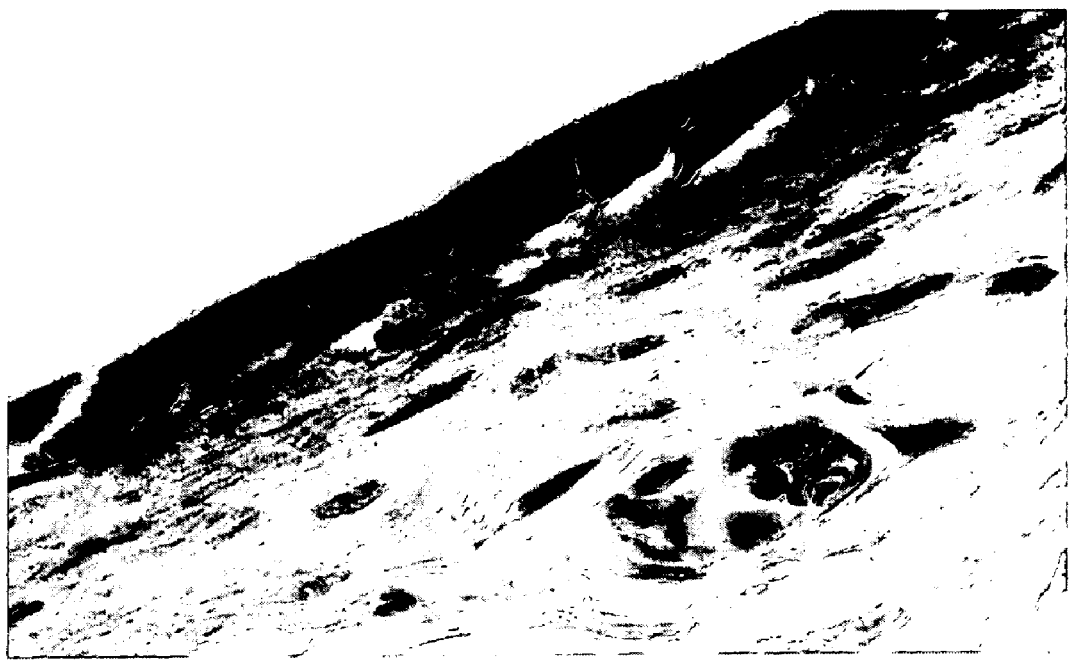
Figure 24A:
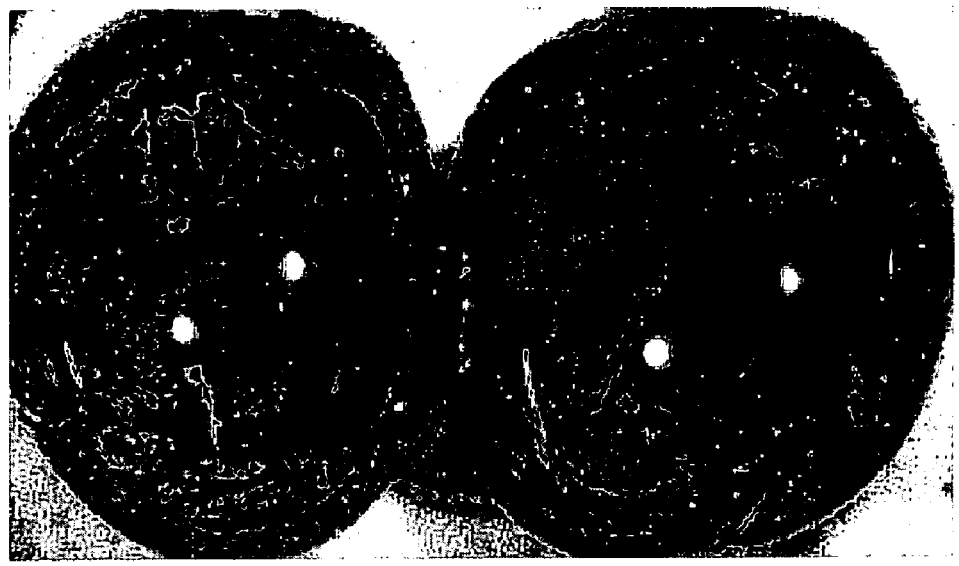
FIG. 24A is a photograph showing the luminal surface of a second murine bladder after pretreatment with a 0.2% polidocanol solution followed by infection with Ad-LacZ.
Figure 24B:
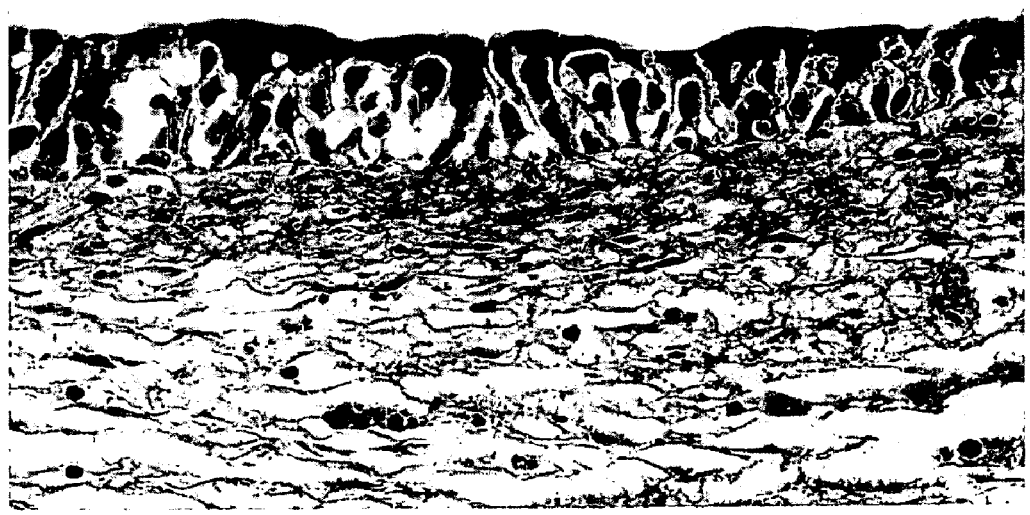
Figure 25A:
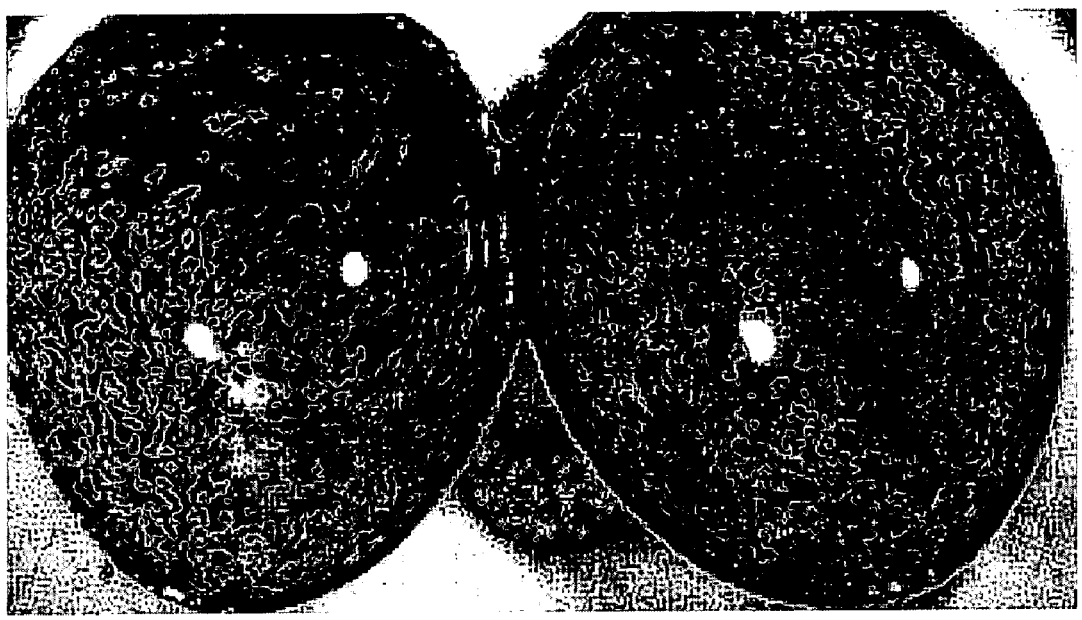
FIG. 25A is a photograph showing the luminal surface of a first murine bladder after pretreatment with a 0.02% n-dodecyl β-D-maltoside solution followed by infection with Ad-LacZ.
Figure 25B:
FIGS. 25B and 25C are photographs showing the cross section of the murine bladder of FIG. 25A wherein FIG. 25B was taken at 40× and FIG. 25C was taken at 100× magnification.
Figure 25C:
Figure 26A:
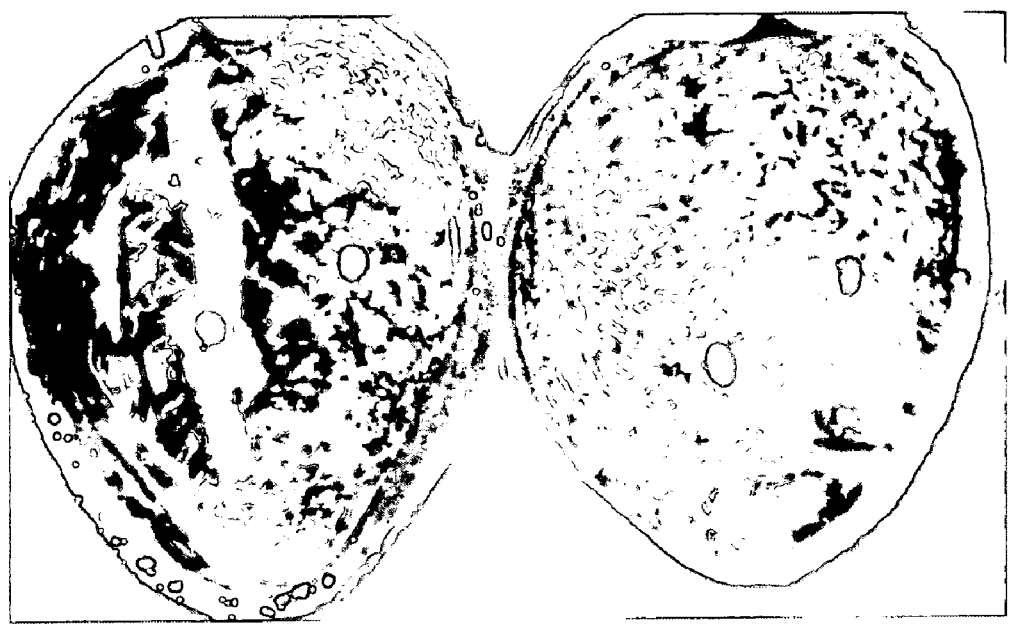
FIG. 26A is a photograph showing the luminal surface of a second murine bladder after pretreatment with a 0.02% n-dodecyl β-D-maltoside solution followed by infection with Ad-LacZ.
Figure 26B:
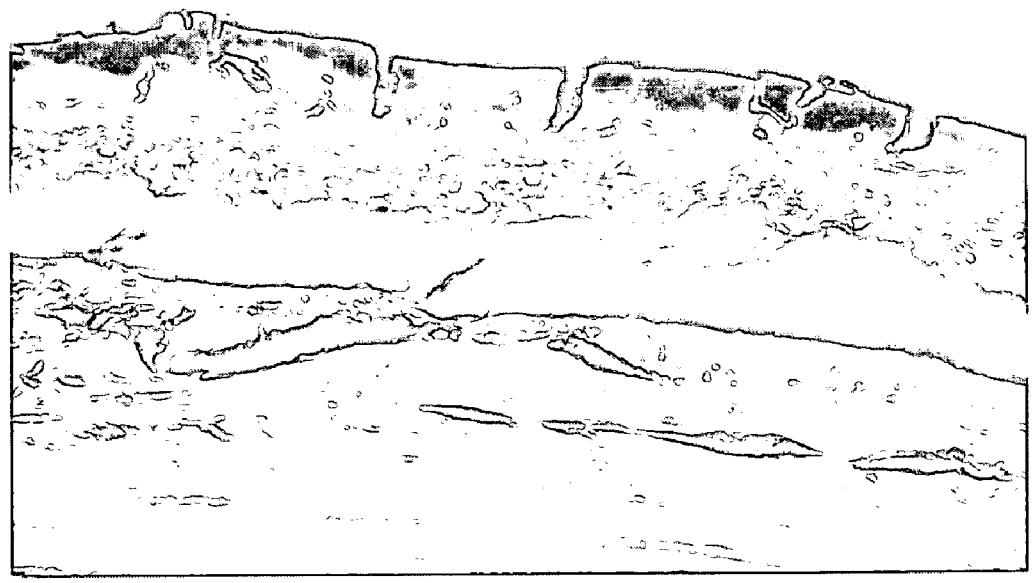
FIGS. 26B and 26C are photographs showing the cross section of the murine bladder of FIG. 26A wherein FIG. 26B was taken at 40× and FIG. 26C was taken at 100× magnification.
Figure 26C:
Figure 27A:
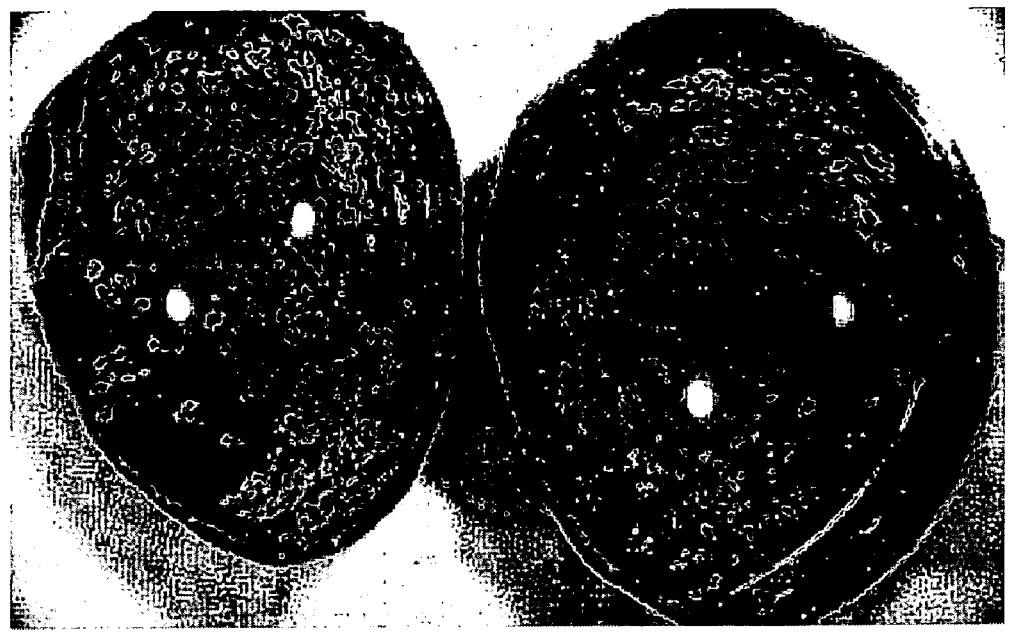
FIG. 27A is a photograph showing the luminal surface of a first murine bladder after pretreatment with a 0.05% n-dodecyl β-D-maltoside solution followed by infection with Ad-LacZ.
Figure 27B:
FIGS. 27B and 27C are photographs showing the cross section of the murine bladder of FIG. 27A wherein FIG. 27B was taken at 40× and FIG. 27C was taken at 100× magnification.
Figure 27C:
Figure 28A:
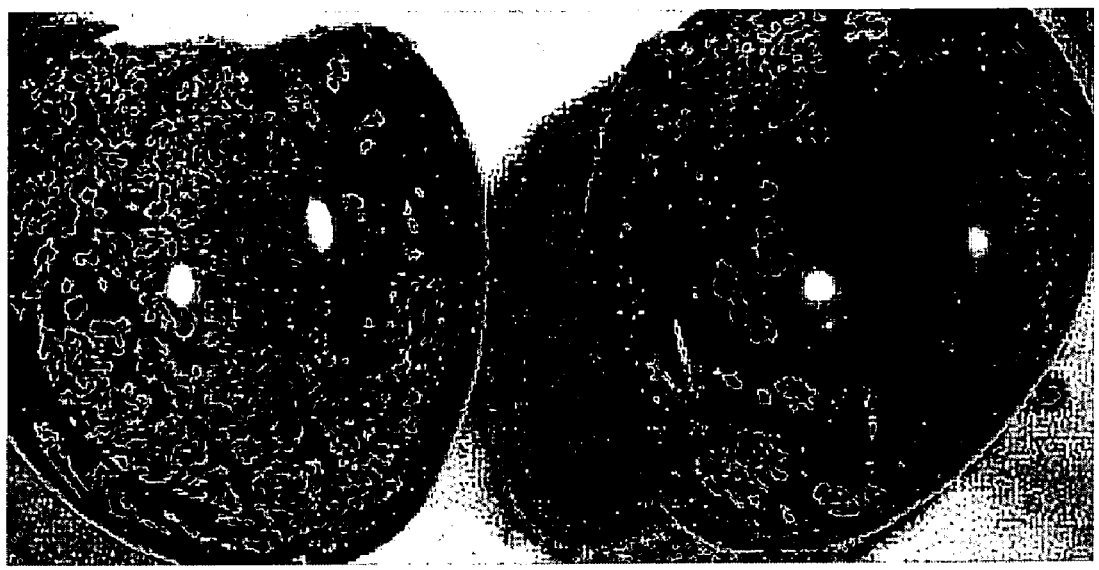
FIG. 28A is a photograph showing the luminal surface of a first murine bladder after pretreatment with a 0.05% n-dodecyl β-D-maltoside solution followed by infection with Ad-LacZ.
Figure 28B:
FIGS. 28B and 28C are photographs showing the cross section of the murine bladder of FIG. 28A wherein FIG. 28B was taken at 40× and FIG. 28C was taken at 100× magnification.
Figure 28C:
Figure 29A:
FIG. 29A is a photograph showing the luminal surface of a first murine bladder after pretreatment with a 0.2% n-dodecyl β-D-maltoside solution followed by infection with Ad-LacZ.
Figure 29B:
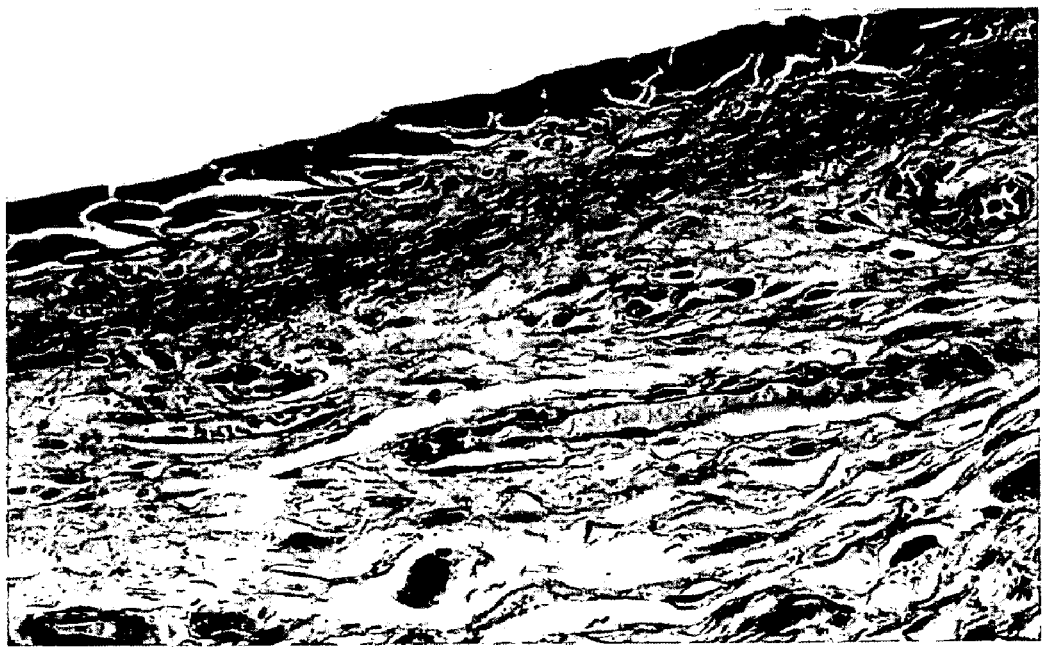
FIGS. 29B and 29C are photographs showing the cross section of the murine bladder of FIG. 29A wherein FIG. 29B was taken at 40× and FIG. 29C was taken at 100× magnification.
Figure 29C:

Results for pretreatment of the bladder surface with 0.2% polidocanol are shown in FIGS. 23 and 24. FIG. 23A is a photograph showing the luminal surface of a first murine bladder after pretreatment with a 0.2% polidocanol solution followed by infection with Ad-LacZ. FIGS. 23B and 23C are photographs showing the cross section of the murine bladder of FIG. 23A. FIG. 23B was taken at 40× and FIG. 23C was taken at 100× magnification. FIG. 24A is a photograph showing the luminal surface of a second murine bladder after pretreatment with a 0.2% polidocanol solution followed by infection with Ad-LacZ. FIGS. 24B and 24C are photographs showing the cross section of the murine bladder of FIG. 24A. FIG. 24B was taken at 40× and FIG. 24C was taken at 100× magnification.

Triton® X-100, having a general formula of:

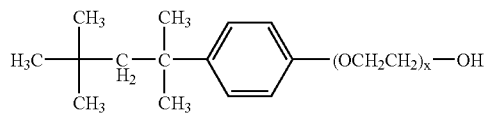

wherein x=10 was also evaluated and was also found to enhance transduction. A similar compound having a cyclohexane ring rather than a benzene ring can also be used as a transduction enhancing agent according to the invention. This compound has the following chemical structure:

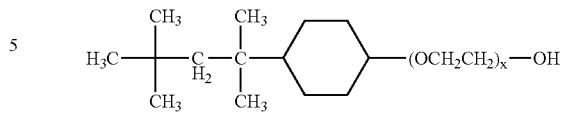

wherein x=10. Compounds of the above type wherein x is any positive integer can also be used according to the invention.

Similar alkyl(ether) compounds having the general structure of:

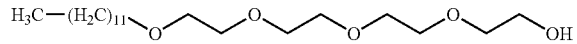

are also commercially available. The trade name for these compounds is "Brij". The compound shown above is designated "Brij 56". Brij 56 has the chemical formula $C_{20}H_{42}O_5$. Another commercially available compound, "Brij 58", has the chemical formula $C_{56}H_{114}O_{21}$.

Any of the above mentioned alkyl(ether) compounds can be used as transduction enhancing agents according to the invention.

Sodium Oxychlorosene

A composition comprising a sodium salt of dodecylbenzenesulfonic acid and hypochlorous acid (i.e., sodium oxychlorosene) at a pH of about 6.5 to 6.9 was evaluated. The sodium oxychlorosene used in these evaluations was sold under the name Clorpactin WCS-90 (manufactured by Guardian Labs and sold by Cardinal Health). Sodium oxychlorosene has been used to treat urinary tract infections and in abdominal and plastic surgery.

Results for pretreatment of the bladder surface with sodium oxychlorosene are shown in FIGS. 8-18. FIGS. 8A-8N are photographs showing seven murine bladders after pretreatment with a 0.2% oxychlorosene solution for 5 minutes followed by infection with Ad-LacZ. FIGS. 8A and 8B show the outside and luminal surfaces, respectively, of the first bladder, FIGS. 8C and 8D show the outside and luminal surfaces, respectively, of the second bladder, FIGS. 8E and 8F show the outside and luminal surfaces, respectively, of the third bladder, FIGS. 8G and 8H show the outside and luminal surfaces, respectively, of the fourth bladder, FIGS. 8I and 8J show the outside and luminal surfaces, respectively, of the fifth bladder, FIGS. 8K and 8L show the outside and luminal surfaces, respectively, of the sixth bladder, and FIGS. 8M and 8N show the outside and luminal surfaces, respectively, of the seventh bladder.

Figure 9A:
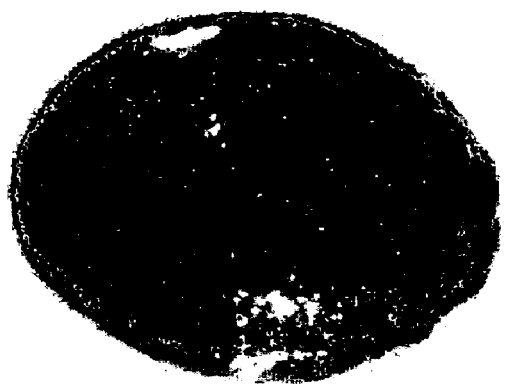
Figure 9B:
Figure 9C:
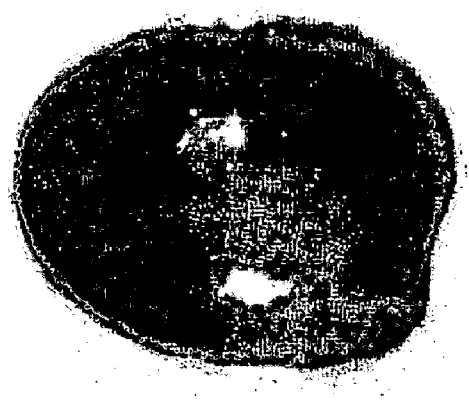
FIGS. 9C and 9D show the outside and luminal surfaces, respectively, of the second bladder.
Figure 9D:
Figure 9E:
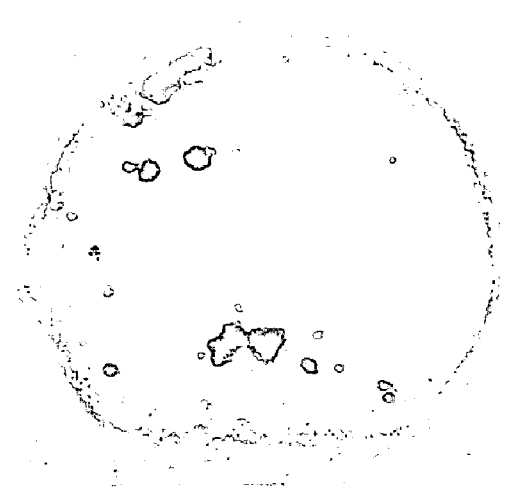
FIGS. 9E and 9F show the outside and luminal surfaces, respectively, of the third bladder.
Figure 9F:
Figure 9G:
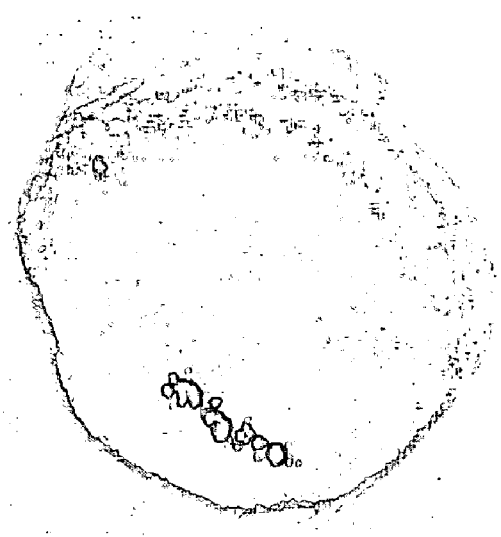
FIGS. 9G and 9H show the outside and luminal surfaces, respectively, of the fourth bladder.
Figure 9H:
Figure 9I:
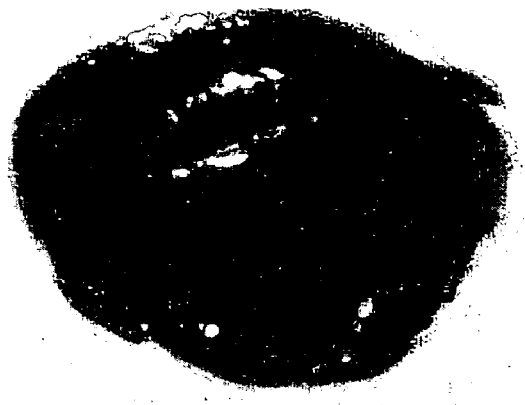
FIGS. 9I and 9J show the outside and luminal surfaces, respectively, of the fifth bladder.
Figure 9J:
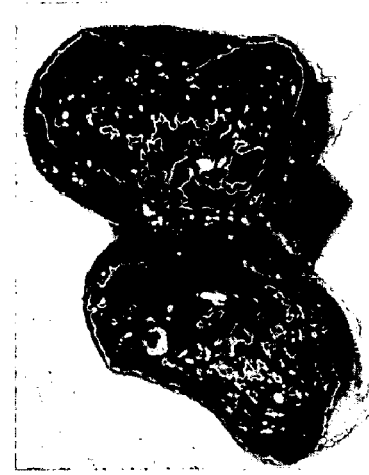
Figure 9K:
FIGS. 9K and 9L show the outside and luminal surfaces, respectively, of the sixth bladder.
Figure 9L:
Figure 9M:
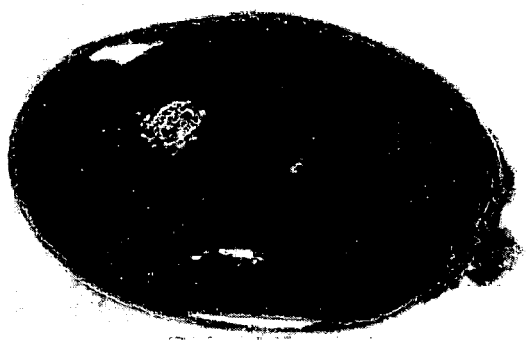
Figure 9N:
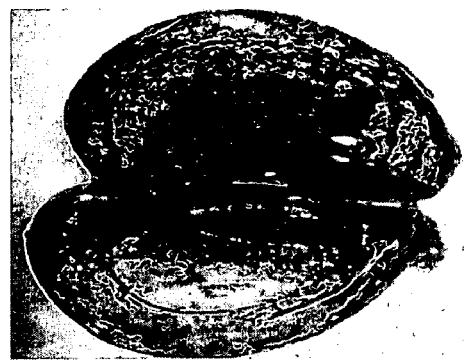

FIGS. 9A-9N are photographs showing seven murine bladders after pretreatment with a 0.2% oxychlorosene solution for 15 minutes followed by infection with Ad-LacZ. FIGS. 9A and 9B show the outside and luminal surfaces, respectively, of the first bladder, FIGS. 9C and 9D show the outside and luminal surfaces, respectively, of the second bladder, FIGS. 9E and 9F show the outside and luminal surfaces, respectively, of the third bladder, FIGS. 9G and 9H show the outside and luminal surfaces, respectively, of the fourth bladder, FIGS. 9I and 9J show the outside and luminal surfaces, respectively, of the fifth bladder, FIGS. 9K and 9L show the outside and luminal surfaces, respectively, of the sixth bladder, and FIGS. 9M and 9N show the outside and luminal surfaces, respectively, of the seventh bladder.

Figure 8A:
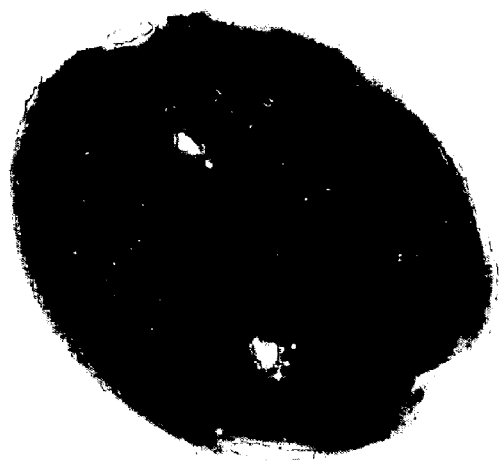
Figure 8B:
Figure 8C:
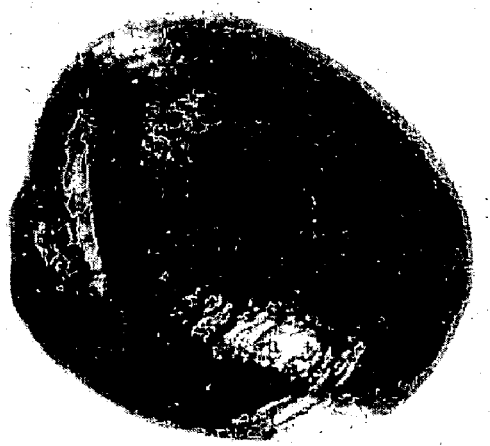
FIGS. 8C and 8D show the outside and luminal surfaces, respectively, of the second bladder.
Figure 8D:
Figure 8E:
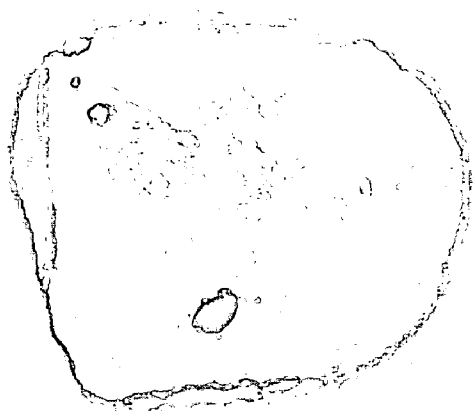
FIGS. 8E and 8F show the outside and luminal surfaces, respectively, of the third bladder.
Figure 8F:
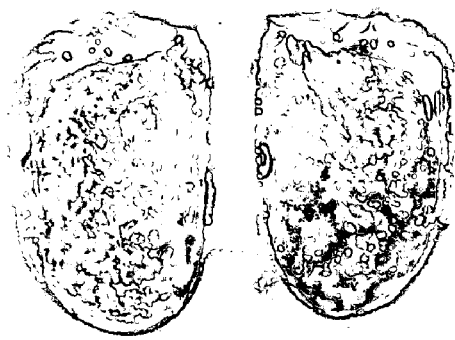
Figure 8G:
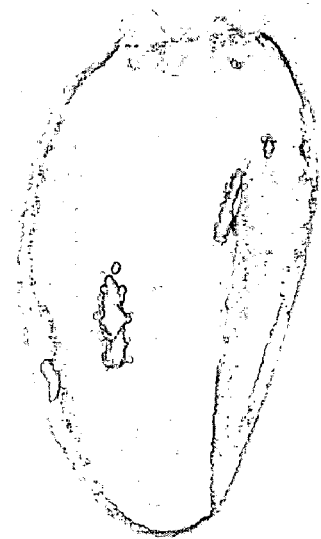
FIGS. 8G and 8H show the outside and luminal surfaces, respectively, of the fourth bladder.
Figure 8H:
Figure 8I:
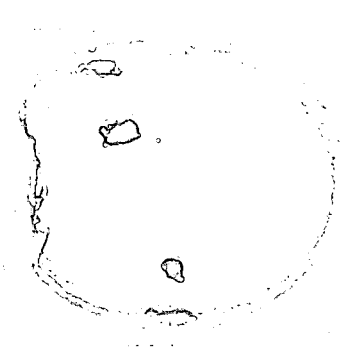
FIGS. 8I and 8J show the outside and luminal surfaces, respectively, of the fifth bladder.
Figure 8J:
Figure 8K:
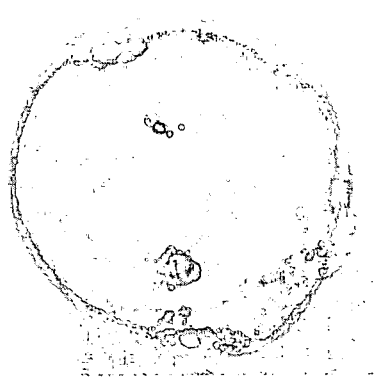
FIGS. 8K and 8L show the outside and luminal surfaces, respectively, of the sixth bladder.
Figure 8L:
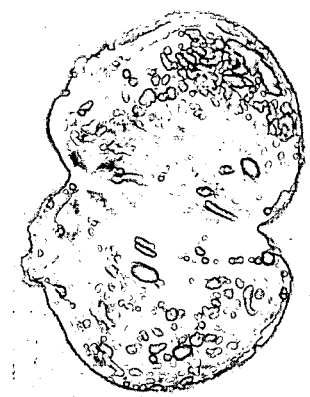
Figure 8M:
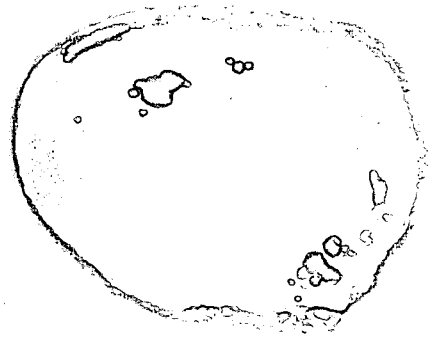
Figure 8N:
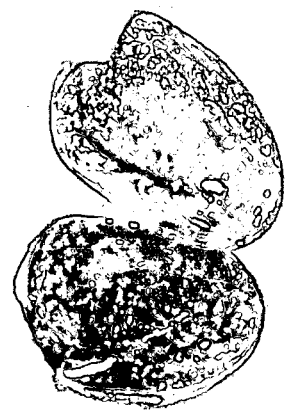
Figure 10A:
FIGS. 10A and 10B are photographs showing the cross section of the murine bladders of FIGS. 8C and 8I, respectively.
Figure 10B:
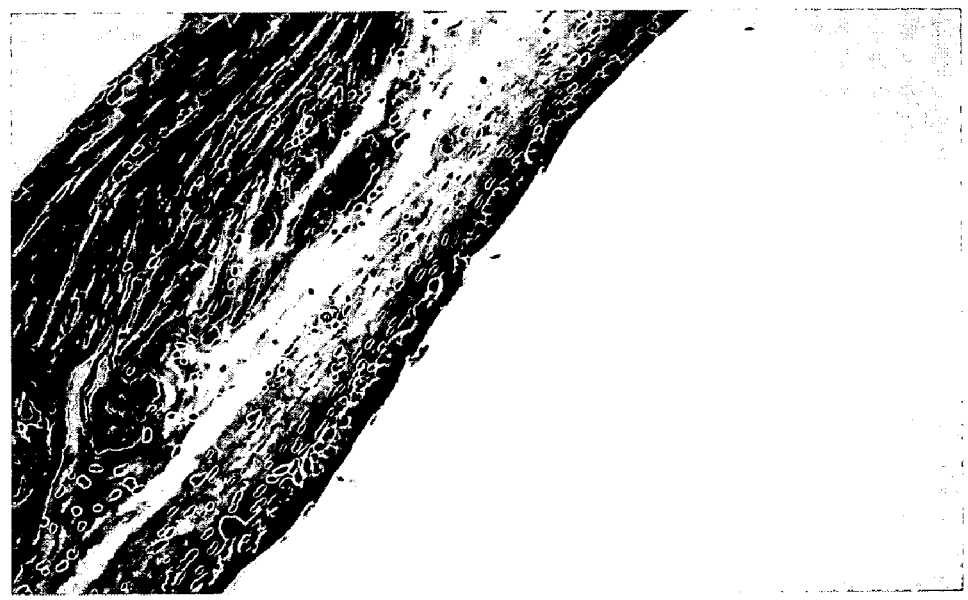
Figure 11A:
FIGS. 11A and 11B are photographs showing the cross section of the murine bladders of FIGS. 9C and 9I, respectively.
Figure 11B:
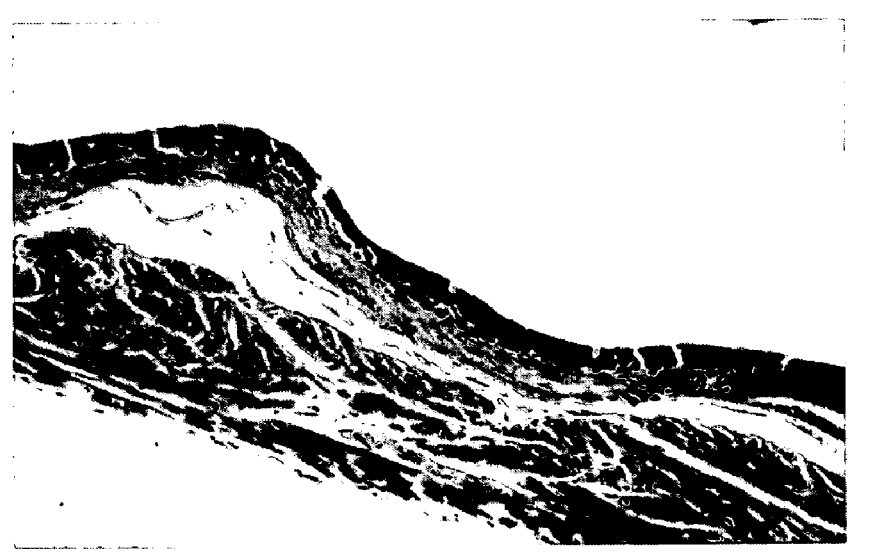

FIGS. 10A and 10B are photographs showing the cross section of the murine bladders of FIGS. 8C and 8I, respectively. FIGS. 11A and 11B are photographs showing the cross section of the murine bladders of FIGS. 9C and 9I, respectively.

Figure 12A:
FIGS. 12A-12F are photographs showing the cross section of a murine bladder after pretreatment with a 0.2% oxychlorosene solution for 5 minutes followed by infection with Ad-LacZ wherein FIGS. 12A, 12C and 12E were taken at 40× and FIGS. 12B, 12D and 12F were taken at 100× magnification.
Figure 12B:
Figure 12C:
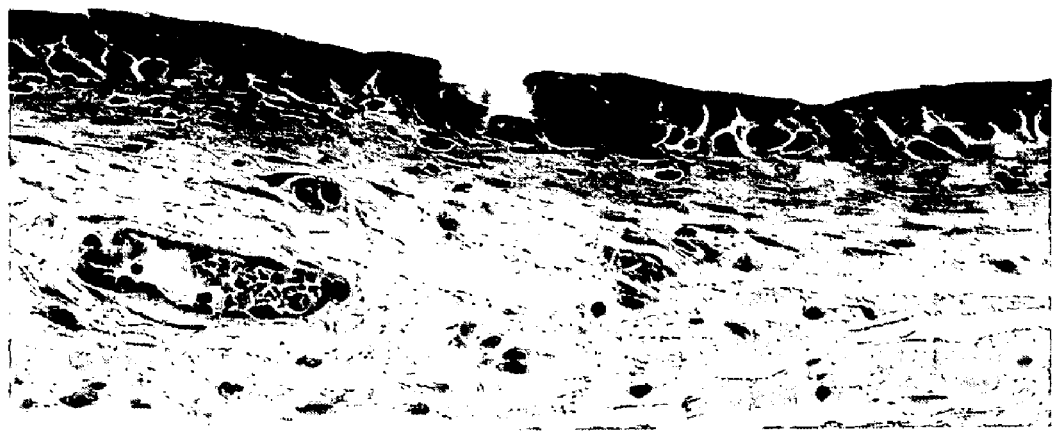
Figure 12D:
Figure 12E:
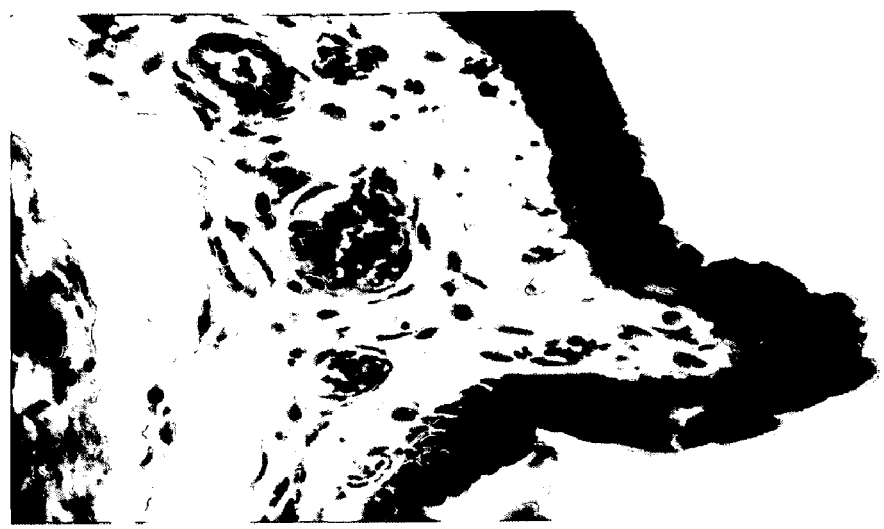
Figure 12F:

FIGS. 12A-12F are photographs showing the cross section of three murine bladders after pretreatment with a 0.2% oxychlorosene solution for 5 minutes followed by infection with Ad-LacZ. FIGS. 12A and 12B are photographs showing the cross-section of the first murine bladder, FIGS. 12C and 12D are photographs showing the cross-section of the second murine bladder, and FIGS. 12E and 12F are photographs showing the cross-section of the third murine bladder. FIGS. 12A, 12C and 12E were taken at 40× and FIGS. 12B, 12D and 12F were taken at 100× magnification.

Figure 13A:
FIGS. 13A-13F are photographs showing the cross section of a murine bladder after pretreatment with a 0.2% oxychlorosene solution for 15 minutes followed by infection with Ad-LacZ wherein FIGS. 13A, 13C and 13E were taken at 40× and FIGS. 13B, 13D and 13F were taken at 100× magnification.
Figure 13B:
Figure 13C:
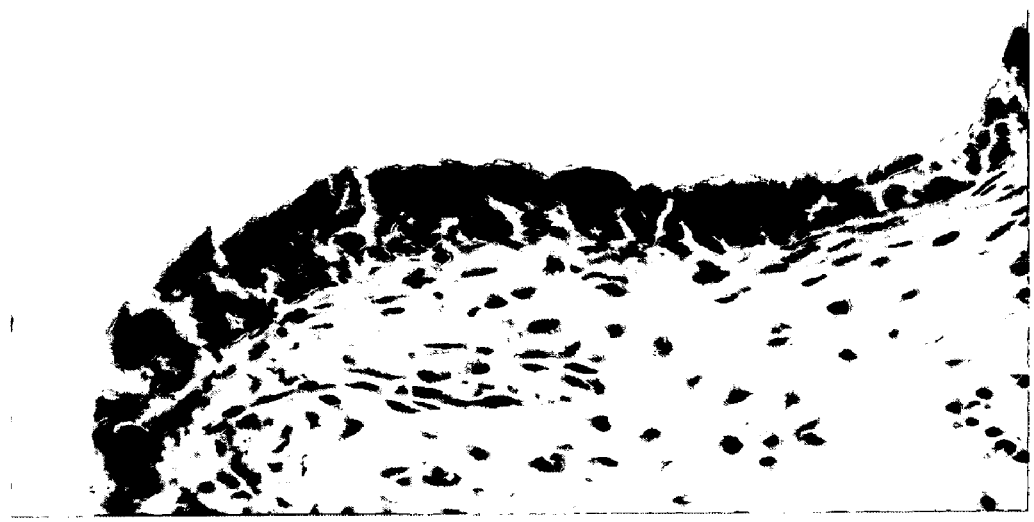
Figure 13D:
Figure 13E:
Figure 13F:
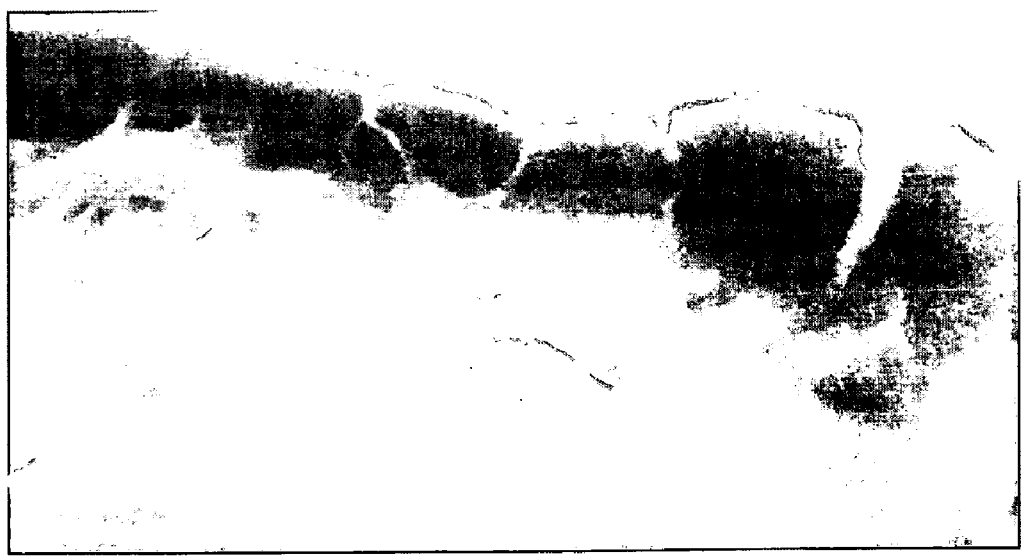

FIGS. 13A-13F are photographs showing the cross section of three murine bladders after pretreatment with a 0.2% oxychlorosene solution for 15 minutes followed by infection with Ad-LacZ. FIGS. 13A and 13B are photographs showing the cross-section of the first murine bladder, FIGS. 13C and 13D are photographs showing the cross-section of the second murine bladder, and FIGS. 13E and 13F are photographs showing the cross-section of the third murine bladder. FIGS. 13A, 13C and 13E were taken at 40× and FIGS. 13B, 13D and 13F were taken at 100× magnification.

Figure 14A:
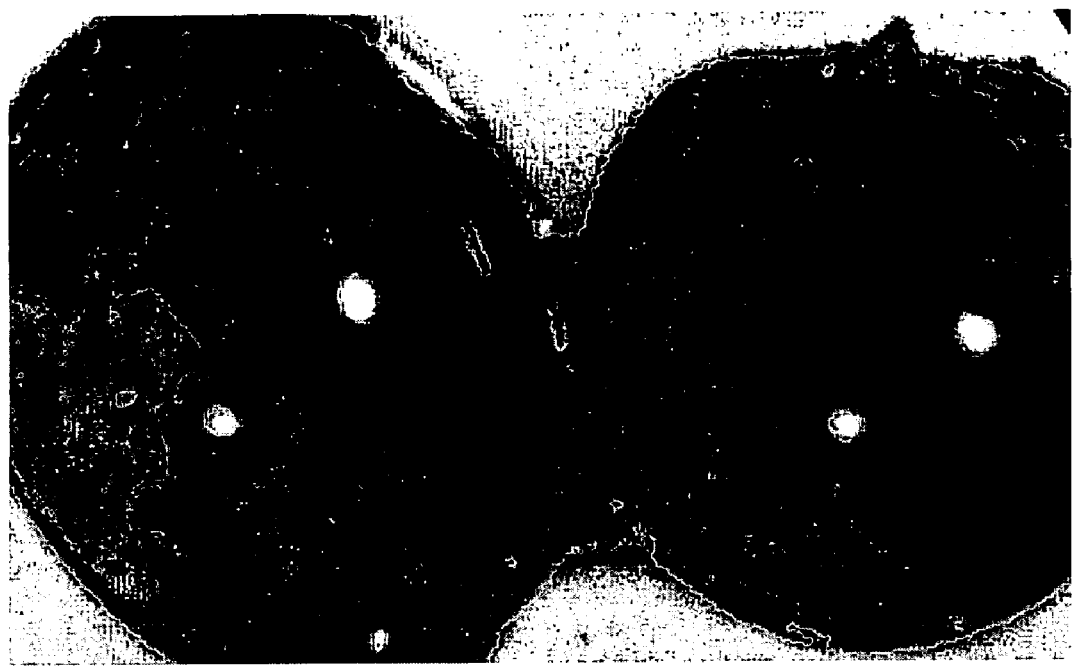
FIG. 14A is a photograph showing the luminal surface of a murine bladder after pretreatment with a 0.1% oxychlorosene solution followed by infection with Ad-LacZ.
Figure 14B:
FIGS. 14B and 14C are photographs showing the cross section of the murine bladder of FIG. 14A wherein FIG. 14B was taken at 40× and FIG. 14C was taken at 100× magnification.
Figure 14C:
Figure 15A:
FIG. 15A is a photograph showing the luminal surface of a first murine bladder after pretreatment with a 0.2% oxychlorosene solution followed by infection with Ad-LacZ.
Figure 15B:
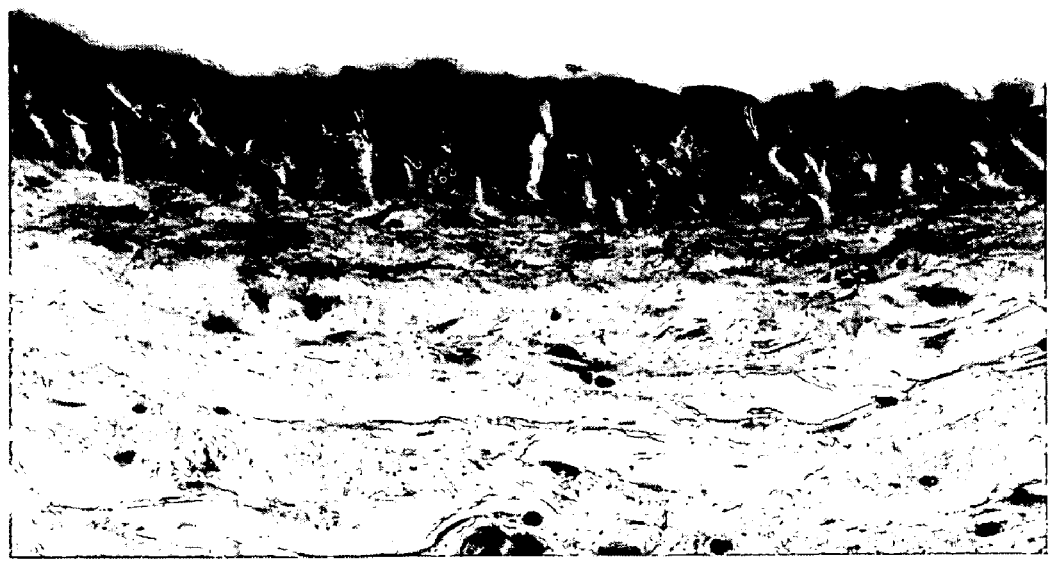
FIGS. 15B and 15C are photographs showing the cross section of the murine bladder of FIG. 15A wherein FIG. 15B was taken at 40× and FIG. 15C was taken at 100× magnification.
Figure 15C:
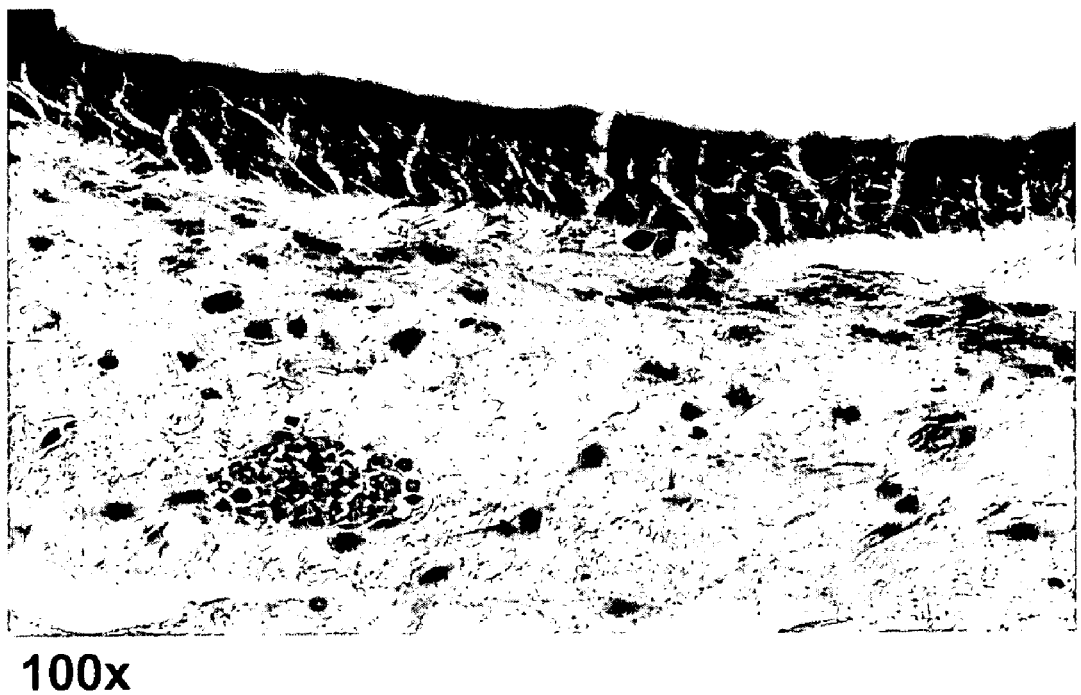

FIG. 14A is a photograph showing the luminal surface of a murine bladder after pretreatment with a 0.1% oxychlorosene solution followed by infection with Ad-LacZ. FIGS. 14B and 14C are photographs showing the cross section of the murine bladder of FIG. 14A. FIG. 14B was taken at 40× and FIG. 14C was taken at 100× magnification;

FIG. 15A is a photograph showing the luminal surface of a first murine bladder after pretreatment with a 0.2% oxychlorosene solution followed by infection with Ad-LacZ. FIGS. 15B and 15C are photographs showing the cross section of the murine bladder of FIG. 15A. FIG. 15B was taken at 40× and FIG. 15C was taken at 100× magnification.

Figure 16A:
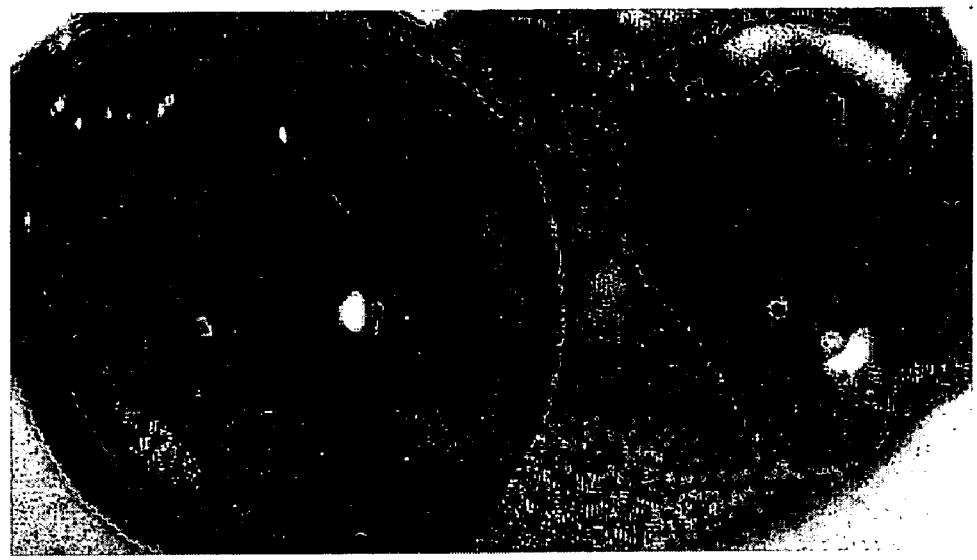
FIG. 16A is a photograph showing the luminal surface of a second murine bladder after pretreatment with a 0.2% oxychlorosene solution followed by infection with Ad-LacZ.
Figure 16B:
FIGS. 16B and 16C are photographs showing the cross section of the murine bladder of FIG. 16A wherein FIG. 16B was taken at 40× and FIG. 16C was taken at 100× magnification.
Figure 16C:

FIG. 16A is a photograph showing the luminal surface of a second murine bladder after pretreatment with a 0.2% oxychlorosene solution followed by infection with Ad-LacZ. FIGS. 16B and 16C are photographs showing the cross section of the murine bladder of FIG. 16A. FIG. 16B was taken at 40× and FIG. 16C was taken at 100× magnification.

Figure 17C:

FIG. 17A is a photograph showing the luminal surface of a first murine bladder after pretreatment with a 0.4% oxychlorosene solution followed by infection with Ad-LacZ. FIGS. 17B and 17C are photographs showing the cross section of the murine bladder of FIG. 17A. FIG. 17B was taken at 40× and FIG. 17C was taken at 100× magnification.

Figure 18A:
FIG. 18A is a photograph showing the luminal surface of a second murine bladder after pretreatment with a 0.4% oxychlorosene solution followed by infection with Ad-LacZ.
Figure 18B:
FIGS. 18B and 18C are photographs showing the cross section of the murine bladder of FIG. 18A wherein FIG. 18B was taken at 40× and FIG. 18C was taken at 100× magnification.
Figure 18C:

FIG. 18A is a photograph showing the luminal surface of a second murine bladder after pretreatment with a 0.4% oxychlorosene solution followed by infection with Ad-LacZ. FIGS. 18B and 18C are photographs showing the cross section of the murine bladder of FIG. 18A. FIG. 18B was taken at 40× and FIG. 18C was taken at 100× magnification.

Polymers with Alternating Hydrophilic and Lipophilic Units

Polymeric compounds comprising repeating sequences of alternating or identical monomers were also tested. One such compound tested was Poloxamer 407 (Pluronic 127) having a structure represented by the following formula:

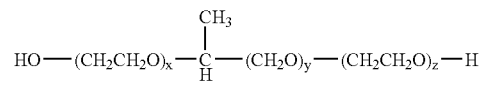

Poloxamers polymers come in a wide range of HLB values. Both of the compounds tested, however, had only a minimal effect on the transduction of adenovirus. While not wishing to be bound by theory, it is believed that compounds having separated, longer hydrophilic and lipophilic chains are more effective at enhancing transduction of the bladder epithelium.

Additional Transduction Enhancing Compounds

Additional compounds can also be used as transduction enhancing agents according to the invention.

These compounds include ω-undecylenyl-β-D-maltopyranoside, which has a structure represented by:

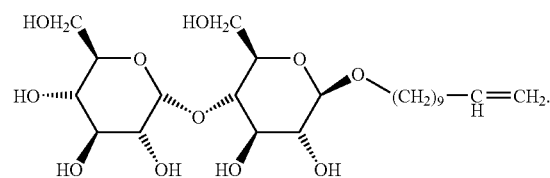

Sugar based thiolic compounds such as alkyl-β-D-thioglucopyranosides having a general structure represented by:

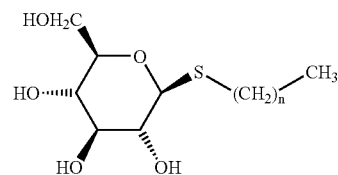

may also be employed.

Additionally, alkyl-β-D-thiomaltopyranosides having a general structure represented by:

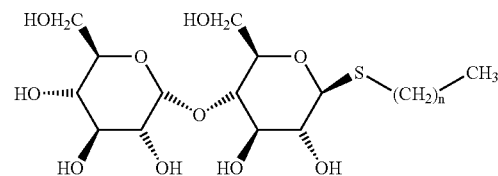

may also be used as transduction enhancing compounds according to the invention.

Further, compounds having a positive charge such as

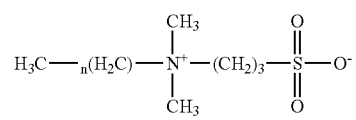

can also be used.

Additionally, compounds wherein the lipophilic and hydrophilic parts are connected via a carboxylic bond can also be employed. An exemplary compound of this type is 6-O-methyl-n-heptylcarboxyl-α-D-glucopyranoside:

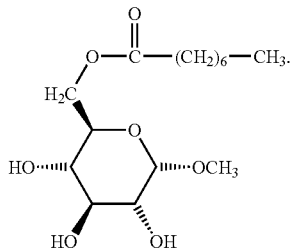

Sugar based compounds having alkyl groups with side groups or other modifications may also be used. Exemplary compounds of this type include 2-propyl-1-pentyl-β-D-maltopyranoside having a structure represented by:

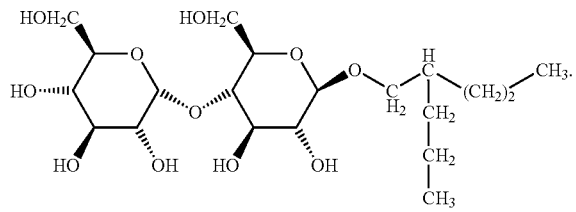

Sarcosine compounds may also be used as transduction enhancing agents according to the invention. Exemplary sarcosine compounds include sodium alkyl sarcosine having a structure represented by:

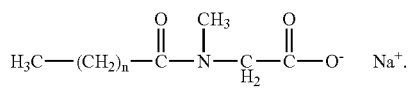

Various substituted sugars can also be used as transduction enhancing compounds. An exemplary substituted sugar which can be used as a transduction enhancing compound is a sucrose mono alkyl ester having a chemical structure represented by:

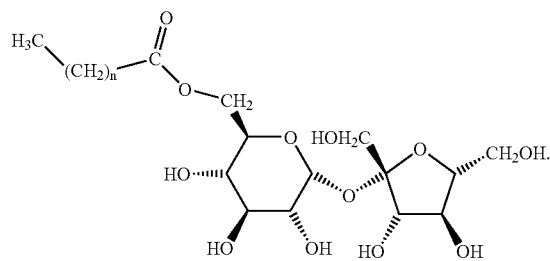

Exemplary compounds of this type include compounds wherein n=10 (i.e., sucrose monolaurate).

Also according to the present invention, methods of treating the luminal surface of the bladder are provided. According to a preferred embodiment of the invention, the bladder is treated by instillation using bladder catheterization. According to this embodiment, any urine in the bladder is first removed and the bladder is optionally washed with a buffer (e.g., PBS). A composition comprising the transduction enhancing agent is then applied to the luminal surface of the bladder (e.g., by instillation). The transduction enhancing solution may be incubated for some specified time or drained immediately. Multiple treatments with the composition comprising the transduction enhancing agent can be performed. After treatment with the transduction enhancing agent, the luminal surface of the bladder may be washed with a buffer (e.g., PBS). A solution comprising the adenovirus can then be introduced into the bladder (e.g., by instillation). The solution comprising the adenovirus can be removed immediately or, alternatively, the solution can be allowed to incubate for a certain amount of time. After treatment with the adenovirus, the bladder surface can again be washed with a buffer solution (e.g., PBS). According to a preferred embodiment of the invention, about 50 to about 500 ml of the transduction enhancing composition is delivered to the bladder by instillation for each treatment.

Alternatively, a composition comprising the transduction enhancing agent and the adenovirus can be used to treat the luminal bladder surface. According to this embodiment of the invention, any urine in the bladder is first removed and the bladder is then optionally washed with a buffer (e.g., PBS). A composition comprising the transduction enhancing agent and the adenovirus is then applied to the luminal surface of the bladder. The solution may be incubated for some specified time or drained immediately. After treatment, the luminal surface of the bladder may again be washed with a buffer (e.g., PBS).

Although phosphate buffered saline (PBS) is the preferred buffer, any other pharmaceutical buffer can be used according to the invention. Exemplary buffers include sodium phosphate/sodium sulfate, Tris buffer, glycine buffer, sterile water and other buffers known in the art, including those described by Good, et al., Biochemistry 5, 467 (1966). The pH of the buffer can be in the range of 6.4 to 8.4, preferably 7 to 7.5, and most preferably 7.2 to 7.4.

The composition comprising the transduction enhancing agent according to the invention preferably also comprises an oxidizing agent. Exemplary oxidizing agents include, but are not limited to, chlorite compounds, hypochlorous acid, hydrogen peroxide, and peroxyacetic acid. According to a preferred embodiment of the invention, any of the single compound transduction enhancing agents can be combined with an oxidizing agent and used as a transduction enhancing agent.

As set forth above, the viral gene therapy vehicle can be an oncolytic virus, for example an oncolytic adenovirus exemplified herein by CG8840. The adenovirus composition can further comprise a chemotherapeutic agent such as Docetaxel. The adenovirus composition preferably comprises from about $1 \times 10^{11}$ to about $1 \times 10^{14}$ viral particles.

Various additional studies were conducted and are described below. In these studies, all percent values that are presented are weight percent values unless otherwise indicated.

Effects of Adenovirus Formulation with Different Concentrations of Dodecyl-β-D-Maltoside on the Infectivity of Mice Bladder Urothlelium Species: Female Balb/c Mouse (Taconic Laboratory)-2/group Study Design: To test the effect of formulating Ad-βgal virus with different concentrations of Dodecyl-β-D-Maltoside and the resultant infection of mice bladder urothelium Dose/Route (Viral Particles #/dose):
   $1 \times 10^{10}$ vp/dose of Ad.CMV.LacZ (Lot# 1351.122)
   0.4%, 0.2%, 0.1%, and 0.05% of n-Dodecyl-β-D-Maltoside (Lot# 100K5308).

An equal volume of 2× DDM and 2× Ad.CMV.LacZ was mixed together immediately before instillation into the bladder. 100 μl of the mixture was instilled into the bladder for 10 min, 20 min, and 45 min.

Endpoints: Bladders were harvested 48 hrs post virus infection with 0.1 ml whole organ fixative (2% Neutral buffered formalin, 2% glutaraldehyde, 2 mM MgCl$_2$, 10 mM PBS, pH 7.4).

Results: Formulating Ad-βgal virus with different concentrations of Dodecyl-β-D-Maltoside resulted in a linear Adenovirus transduction rate (0.1%>0.05%>0.025%). For the 20 min. instillation, 0.1% DDM formulated with Ad-βgal virus resulted in about 80% gene expression in bladder, while 0.05% DDM resulted in about 40% gene expression. But with 45 min. instillation, all animals with 0.05%-0.2% DDM with Ad-βgal virus had 100% gene expression in mice bladder. A 10 min. instillation for this formulation method, however, did not achieve an acceptable transduction rate. It was also found that gene transduction could be achieved with a 10 min. virus instillation after DDM pretreatment.

This study illustrates that DDM can be formulated with Ad-βgal virus in mice bladder model. Further, with a DDM pretreatment, the time for virus instillation can be decreased to 10 min. from 45 min.

Effects of Different Diluents on the Infectivity of Mice Bladder Urothelium by Adenovirus Species: Female Balb/c Mouse (Taconic Laboratory)—2/group Study Design: To test the effects of different diluents on Adenovirus infectivity of mice urothelium followed DDM pretreatment (QQ5 minQ). The virus would be diluted 100 fold with the diluents prior to instillation into mice bladder for 45 min.

Dose/Route:
   $1 \times 10^{9}$ vp/dose of Ad.CMV.LacZ (Lot #1351.122)
   Dodecyl-β-D-Maltoside (Lot #100K5308).

Diluents (A): 0.9% Sodium Chloride Injection Solution (Baxter Lot# 1A1322); (B): 2.5% Dextrose and 0.45% Sodium Chloride Injection Solution (Baxter Lot# C529040); and (C): Plasma-lyte A Injection Solution pH 7.4 (Baxter Lot# C558106); and ARCA buffer.

Endpoints: Bladders were harvested 48 hrs post virus infection with 0.1 ml whole organ fixative (2% Neutral buffered formalin, 2% glutaraldehyde, 2 mM MgCl$_2$, 10 mM PBS, pH 7.4).

Results: There were no significant differences in Ad-βgal gene expression levels between mice bladder receiving virus diluted with different diluents. All the animals had >90% in Ad-βgal gene expression in mice bladder.

Adenovirus Dose Titration with Different Chemical Agents Pretreatment on SD Rat Bladder Epithelium Species: Female Sprague Dawley Rat (Taconic Laboratory)—2/group Study Design: To test the virus infectivity of rat bladder epithelium with different doses of Adenovirus following the pretreatment with SDS or DDM. This study also explored relationship between bladder volume and residual of SDS or DDM for adenovirus infectivity.

Dose/Route:
   $4 \times 10^{9}$ and $4 \times 10^{1}$ vp/dose of Ad.CMV.LacZ (Lot# 1351.122)
   0.1% Dodecyl-β-D-Maltoside (Lot#100K5308)
   0.1% SDS (Integra Lot# 836011 and Lot# BK14J11)
   400 μl of SDS or DDM was instilled into bladder (QQ5 minQ) followed by six PBS washes, then Adenovirus for 15 min.

Endpoints: Bladders were harvested 48 hrs post virus infection with 0.2 ml whole organ fixative (2% Neutral buffered formalin, 2% glutaraldehyde, 2 mM MgCl$_2$, 10 mM PBS, pH 7.4).

Results: There were no significant differences in Ad-βgal gene expression levels between rat bladders pretreated with different lot of SDS and DDM. Rat bladders infected with $4 \times 10^{10}$ vp adenovirus achieved >90% Ad-βgal gene expression levels whereas rat bladders infected with $4 \times 10^{9}$ vp adenovirus had Ad-βgal gene expression levels range from 30% to 50%. It was found that rat bladder needed 10 times more adenovirus to achieve similar Ad-βgal gene expression levels compared with mouse bladder. SDS and DDM pretreatment were both effective to remove GAG layer of bladder epithelium.

Efficacy of Dodecyl-β-D-Maltoside as a Pretreatment Agent Prior to Adenovirus Infection of Mice Bladder Urothelium Species: Female Balb/c Mouse (Taconic Laboratory)—2/group Study Design: To test DDM from two different suppliers as pretreatment agents to enhance the adenovirus infection of mice bladder urothelium in a large group of animals.

Dose/Route:
   $1 \times 10^{10}$ vp/dose of Ad.CMV.LacZ (Lot #1351.122)
   Dodecyl-β-D-Maltoside (Lot # 018H7250 and Lot # P21/39/092)
   100 μl of DDM was instilled into bladder (QQ5 minQ) followed by three PBS washes, then Adenovirus for 15 min.

Endpoints: Bladders were harvested 48 hrs post virus infection with 50 μl whole organ fixative (2% Neutral buffered formalin, 2% glutaraldehyde, 2 mM MgCl$_2$, 10 mM PBS, pH 7.4).

Results: There were no significant differences in Ad-βgal gene expression levels between mice bladder pretreated with these two different lots of DDM. In each case, >90% Ad-βgal expression was achieved. Therefore, DDM from either manufacturer is a good candidate for a chemical enhancer for adenovirus infection in mice bladder.

Efficacy of Dodecyl-β-D-Maltoside as Chemical Enhancer Prior to Adenovirus Infection of SW780+ Luc Orthotopic Bladder Tumor Model in Mice Species: Female NCR nu/nu Mouse (Taconic Laboratory)-2/group Study Design: To show DDM pretreatments enhance Ad.Lac Z infectivity in mice bladder urothelium. To further confirm the enhancer effect on orthotopic tumors, two mice bearing orthotopic SW780 bladder tumors were pretreated with or without DDM (QQ5 minQ) followed by 15 min Ad.Lac Z instillation. The Ad.Lac Z gene expression levels were checked in these tumor cells 4 days post Ad.Lac Z infection.

Dose/Route:
   $1 \times 10^{10}$ vp/dose. Ad.CMV.LacZ Lot# 1351.122.
   Dodecyl-β-D-Maltoside (Lot#018H7250).
   100 μl of DDM was instilled into bladder (QQ5 minQ) followed by three PBS washes, then Adenovirus for 15 min.

Endpoints: Bladders were harvested 96 hrs post virus infection with 50 μl whole organ fixative (2% Neutral buffered formalin, 2% glutaraldehyde, 2 mM $MgCl_2$, 10 mM PBS, pH 7.4). Results: There was a significant difference in Ad-βgal gene expression levels between mice bladders pretreated with DDM and control animals. Without DDM pretreatment, there was very low Ad-βgal gene expression levels in bladder epithelium cells and tumor cells. With DDM pretreatment, nearly 100% of the epithelium cells were transduced with Ad-βgal gene in bladder tumors except those dead necrotic tumor cells. It was concluded that DDM pretreatment enhances Adenovirus infection in orthotopic tumor cells.

Testing of DDM and SDS Subgroup Compounds Containing Different Lengths of Alkyl Side Chain and Different Types of Sugar Molecule as Pretreatment Agents Prior to Adenovirus Infection of Mouse Bladder Urothelium Species: Female Balb/c Mouse (Taconic Laboratory)—3-2/group Study Design: Several compounds belonging to the Dodecyl-β-D-Maltoside (DDM) and Sodium Dodecyl Sulfate (SDS) subgroups containing different lengths of alkyl side chain and different sugar molecules were tested as pretreatment agents to enhance the adenovirus infection of mouse bladder epithelium. All compounds were dissolved in PBS at 0.1% concentration.

Dose/Route:
$1\times10^9$ vp/dose. Ad.CMV.LacZ (Lot #1351.122)
0.1% Dodecyl-β-D-Maltoside (Lot #P21/39/092) and 0.1% SDS (Lot #101K0036) were the positive controls for this study.

100 µl of Ad-βgal virus was instilled into bladder via intravesicle administration for 15 min followed different chemicals pretreatment (QQ5 minQ).

Endpoints: Bladders were harvested 48 hrs post virus infection with 50 µl whole organ fixative (2% Neutral buffered formalin, 2% glutaraldehyde, 2 mM $MgCl_2$, 10 mM PBS, pH 7.4).

Results: For the DDM subgroup compounds, compounds with alkyl side chain lengths longer than C12 had the best enhancer ability. DDM subgroup compounds having C8, C10, C12, C13 and C14 alkyl side chains were evaluated. For the SDS subgroup compounds, compounds with alkyl side chain lengths shorter than C12 had very low Ad-βgal gene expression levels. SDS subgroup compounds having C8, C10 and C12 alkyl side chains were evaluated.

The type of sugar molecule did not appear to have a significant effect on the efficacy of these compounds as pretreatment enhancers with the exception of sucrose monolaurate. While not wishing to be bound by theory, we believe that the disaccharide chain could enhance adenovirus infectivity based on currently available data.

Pilot Efficacy Study: CG8840 Treatment with SW780+Luc Orthlotopic Bladder Tumor Model in Mice Species: Female NCR nu/nu Mouse (Taconic or Simonsen Laboratory)-6/group for CG8840 and 3/group for CG7870

Study Design: To test the efficacy of bladder specific oncolytic virus CG8840 alone with prostate specific oncolytic virus CG7870. Two treatment regimens were used for CG8840: $1\times10^{10}$ and $1\times10^8$ vp/dose. One treatment regimen was used for for CG7870: $1\times10^{10}$ vp/dose. One dose of virus would be delivered into bladder weekly for the consecutive three weeks.

Dose/Route:
1 million SW780tLuc cells Clone #19 (P4)
CG8840 Lot# 1408.190; CG7870 (Lot # 38.145)
0.1% Dodecyl-β-D-Maltoside (Lot #018H7250).

15 mg/ml Luciferin (Xenogen cat# XR-1001) substrate solution was made in PBS filtered with 0.2 µM filters.

120 µl of $1\times10^7$ cell/ml SW780+luc cells were aliquot into each tube and kept in ice before instillation. One aliquot for each mice bladder.

Endpoints: Live image mice bladder was performed weekly for 10 weeks. H & E stain and Human Cytokeratin Stain were performed on those available bladder and kidney samples.

Results: There were significant differences in reducing tumor volumes between CG8840 ($1\times10^{10}$ vp/dose) treated mice and control animals (both CG7870 and no virus treated groups). Three out of six mice treated with $1\times10^{10}$ vp/dose CG8840 had completed tumor regression after second dose instillation and kept tumor free until the end of the study (week 10). Human cytokeratin stain showed there were no tumor cells in those mouse bladders. Efficacy for $1\times10^8$ vp/dose of CG8840 was not significant, there was a one out of five mouse had incomplete tumor regression on week 5 and kept tumors at bay to the end. Tumor metastasis to kidney is a significant threat to tumor bearing mice survival. Any mice with kidney metastasis would soon die even if they were free of bladder tumors.

CG8840 Treatment with SW780+Luc Orthotopic Bladder Tumor Model in Mice

Species: Female NCR nu/nu Mouse (Taconic Laboratory)—10/group

Study Design: This study was designed to observe the efficacy of bladder specific oncolytic virus CG8840 treatment modality for bladder tumors. CG8840 virus was instilled into the bladder via intravesical administration for 15 min and 30 min, respectively. To reduced kidney tumor metastasis, two different DDM pretreatment procedures were tested during SW780 tumor cell implanting: (1) 0.1% DDM QQ5 minQ; and (2) 0.1% DDM Q10 min.

Dose/Route:
1 million SW780+Luc cells Clone #19 (P4).
CG8840 Lot# 1408.190. 0.1% Dodecyl-β-D-Maltoside (Lot #018H7250).
15 mg/ml Luciferin (Xenogen cat# XR-1001) substrate solution was made in PBS filtered with 0.2-µM filters.

90 µl of $1.1\times10^7$ cell/ml SW780+luc cells were aliquot into each tube and kept in ice before instillation. One aliquot for each mice bladder.

Endpoints: Live imaging of the mice bladders was performed weekly for 8 weeks. H & E stain and Human Cytokeratin Stain were performed on those available bladder and kidney samples.

Results: There were significant difference in reducing tumor volumes between CG8840 (15 min. and 30 min. virus treatment) treated mice and control animals. In particular, seven out of nine mice with 15 min. virus treatment showed significant tumor volume regression after first virus treatment. Five of them were tumor free till the end of the study. The CG8840 treatment with three doses of $1\times10^{10}$ vp/dose injected in three consecutive weeks proved very effective to eradicate orthotopic SW780 tumors in mouse bladder. However, longer virus instillation times (i.e., in excess of 15 min.) do not appear to increase virus copy numbers within tumor cells.

For SW780 tumor cell implantation, 0.1% DDM pretreatment with Q10 min. washes, less kidney tumor metastasis was observed in mice with orthotopic tumors.

Varius additional studies were conducted to determine adenovirus compatibility with various reagents. These studies are described below.

Study #1—Compatibility of Ad5-LacZ with Ethanol and Urine

In this study, each sample was incubated at 37° C. for one hour before the plaque assay started. The data for this study are shown below in Table 3.

TABLE 3

Adenovirus stability after incubation (EtOH, urine)

| Sample Name | Titer vp/mL | Average pfu/mL | Stdev. | Ratio vp/pfu |
|---|---|---|---|---|
| Ad5-Lac Z in ARCA | 1.30E+12 | 5.85E+10 | 1.49E+10 | 22.23 |
| Ad5-Lac Z in ARCA 40% EtOH | 7.80E+11 | 6.36E+07 | 1.68E+07 | 12255.34 |
| Ad5-Lac Z in ARCA 5% EtOH | 1.24E+12 | 5.07E+10 | 0.00E+00 | 24.47 |
| Ad5-Lac Z in ARCA 1:100 Urine | 1.30E+10 | 6.26E+08 | 2.55E+08 | 20.75 |
| Ad5-Lac Z −80° C. | 1.30E+12 | 5.90E+10 | 9.28E+09 | 22.04 |
| R-06-80 1 Hr. Hold | 6.00E+11 | 2.34E+10 | 2.76E+09 | 25.65 |
| R-06-81 | 6.00E+11 | 3.12E+10 | 8.27E+09 | 19.24 |

This data indicates that Ad-LacZ does not lose its activity after incubation with urine, 5% ethanol, or ARCA at biological temperature. However, 40% ethanol inactivated most of the virus.

Study #2: Compatibility of Ad5-LacZ with Ethanol

For this study, each sample was incubated at 37° C. before the plaque assay started. The data for this study are shown below in Table 4.

TABLE 4

Adenovirus Stability after Incubation (EtOH, PBS)

| Sample Name | Titer vp/mL | Average pfu/mL | St. dev. | Ratio vp/pfu |
|---|---|---|---|---|
| Ad 5 Lac Z | 1.30E+12 | 4.34E+10 | 7.58E+09 | 30 |
| Ad 5 Lac Z in PBS | 1.30E+11 | 5.43E+09 | 4.26E+08 | 24 |
| PBS/10% EtOH | 1.30E+11 | 3.72E+09 | 4.26E+08 | 35 |
| PBS/20% EtOH | 1.30E+11 | 1.81E+09 | 2.84E+08 | 72 |
| PBS/30% EtOH | 1.30E+11 | <1.1E+5 pfu/mL | | |
| 1230-054 | 1.00E+11 | 9.55E+08 | 2.13E+08 | 105 |
| R-06-80 | 6.00E+11 | 1.90E+10 | 6.20E+09 | 32 |

The above results indicate that higher concentrations of ethanol (i.e., ≧10%) will result in partial to complete inactivation of adenovirus.

Study #3—Compatibility of Adenovirus with Selected Enhancers

For this study, each sample was incubated at 37° C. or 25° C. before the plaque assay started. The data for this study are shown below in Table 5.

TABLE 5

Adenovirus Stability after Incubation with Selected Enhancer Solutions

| Solution | Temp | Incub. Time | Titer vp/mL | Average pfu/mL | St. Dev. | Ratio vp/pfu |
|---|---|---|---|---|---|---|
| None | 5° C. | none | 4.23E+11 | 1.95E+10 | 0.00E+00 | 22 |
| Oxychlorosene | 37° C. | 1 hour | 2.12E+11 | 8.82E+05 | 1.56E+05 | 240287 |
| Dodecyl Maltoside | 37° C. | 1 hour | 2.12E+11 | 1.36E+10 | 1.38E+09 | 16 |
| Polidocanol | 37° C. | 1 hour | 2.12E+11 | 1.22E+10 | 2.07E+09 | 17 |
| Oxychlorosene | 25° C. | 2 hours | 2.12E+11 | 2.18E+08 | 0.00E+00 | 974 |
| Dodecyl Maltoside | 25° C. | 2 hours | 2.12E+11 | 1.32E+10 | 6.89E+08 | 16 |
| Polidocanol | 25° C. | 2 hours | 2.12E+11 | 1.02E+10 | 4.82E+09 | 21 |
| none | −70° C. | none | 6.00E+11 | 2.76E+09 | 2.13E+08 | 21.7 |

As can be seen from the above data, dodecyl maltoside and polidocanol are compatible with the adenovirus under the experimental conditions while oxychlorosene can inactivate the virus by increase in temperature and time of incubation.

Study #4—Degradation of Adenovirus by Sodium Dodecyl Sulfate (SDS)

A series of experiments were preformed on samples of adenovirus incubated at 37° C. for 15-30 minutes in various concentrations of SDS. The resulting material was examined by anion exchange chromatography. It was confirmed that concentrations of SDS above or equal to 0.025% SDS will rapidly degrade the virus. SDS at 0.0125% did not reduce the particle quality or quantity by AEX method after 30 minutes of incubation.

Study #5—Degradation of Adenovirus by Sodium Dodecyl Sulfate (SDS)

In this study, adenovirus (Ad-LacZ) preparations (1.0× $10^{12}$ vp/ml) were mixed with solutions of SDS or DDM to obtain a mixture of adenovirus and each of these surfactants. Final concentrations of SDS or DDM were 0.1% and the virus had a 5.0×$10^{11}$ vp/ml as the result of mixing. These samples were incubated at 25° C. or 37° C. for one hour before freezing. They were sent to assay services for plaque assay analysis. The results for this study are shown below in Table 6.

TABLE 6

Adenovirus Stability after Incubation with 0.1% SDS or 0.1% DDM Solutions

| Sample ID | Replicate | Titer | Mean Titer PFU/mL |
|---|---|---|---|
| Ad-LacZ 1351-122 | 1 | 3.70E+10 | 4.85E+10 |
| | 2 | 6.00E+10 | |
| Ad-LacZ ARCA 1 Hr 25° C. | 1 | 2.05E+10 | 2.05E+10 |
| Ad-LacZ ARCA 1 Hr 37° C. | 1 | 2.15E+10 | 2.15E+10 |
| Ad-LacZ DDM 1 Hr 25° C. | 1 | 3.25E+10 | 3.25E+10 |
| Ad-LacZ DDM 1 Hr 37° C. | 1 | 3.55E+10 | 3.55E+10 |

TABLE 6-continued

Adenovirus Stability after Incubation with 0.1% SDS or 0.1% DDM Solutions

| Sample ID | Replicate | Titer | Mean Titer PFU/mL |
|---|---|---|---|
| Ad-LacZ SDS 1 Hr 25° C. | 1 | no activity | no activity |
| Ad-LacZ SDS 1 Hr 37° C. | 1 | no activity | no activity |

This experiment confirmed that a relatively short exposure of adenovirus at elevated temperatures to SDS solutions will inactivate the virus. However, the DDM solution had no adverse effects on adenovirus.

The following table (Table 7) summarizes the transduction efficacy of exemplary pretreatment agents. In Table 7, transduction efficacy is defined as follows: "0" means 0-10% transduction efficacy; "+" means 10-25% transduction efficacy; "++" means 25-50% transduction efficacy; "+++" means 50-75% transduction efficacy; and "++++" means >75% transduction efficacy.

TABLE 7

Transduction Efficacy of Exemplary Pretreatment Agents

| Pretreatment Agent | Transduction Efficacy |
|---|---|
| Alkyl disaccharides | |
| n-Dodecyl-β-D-Maltoside (C12) | ++++ |
| n-Dodecyl-α-D-Maltoside (C12) | ++++ |
| Sucrose monolaurate (C12) | ++++ |
| 6-Cyclohexylhexyl-b-D-Maltoside | ++++ |
| n-Tridecyl-β-D-Maltoside (C13) | +++ |
| n-Tetradecyl-β-D-Maltoside (C14) | ++ |
| n-Decyl-β-D-Maltoside (C10) | + |
| n-Octyl-β-D-Maltoside (C8) | (0) |
| Alkyl sulfate (ionic Alkyl) | |
| Sodium dodecyl sulfate (C12) | ++++ |
| Sodium decyl sulfate (C10) | + |
| Sodium octyl sulfate (C8) | (0) |
| Sodium tetradecyl sulfate (C14) | (0) |
| Na salt of dodecyl benzenesulfonic acid | + |
| Alkyl (ether) alcohols | |
| Polidocanol | ++ |
| Polymeric surfactants | |
| Triton X-100 | + |
| Poloxamers F68, F127 | (0) |
| Tween 20, Tween 80 | (0) |

While the foregoing specification teaches the principles of the present invention, with examples provided for the purpose of illustration, it will be appreciated by one skilled in the art from reading this disclosure that various changes in form and detail can be made without departing from the true scope of the invention.

All publications cited herein are hereby incorporated by reference in their entirety.

What is claimed is:

1. A method for treating superficial cancer of the bladder derived from the bladder epithelium, comprising:
   contacting the luminal surface of the bladder with a pretreatment composition comprising a transduction enhancing agent; and
   further contacting the luminal surface of the bladder with a composition comprising a replication competent oncolytic virus;
   wherein cells of the bladder epithelium are transduced and the transduction enhancing agent has the following general formula (I):

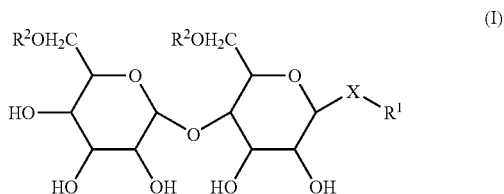

wherein X is a sulfur or oxygen atom, each $R^2$ is independently hydrogen or a moiety represented by:

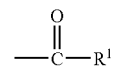

and $R^1$ represents an alkyl or alkenyl group of 12 carbons.

2. The method of claim 1, wherein each $R^2$ is hydrogen.

3. The method of claim 1, wherein the transduction enhancing agent has the chemical formula:

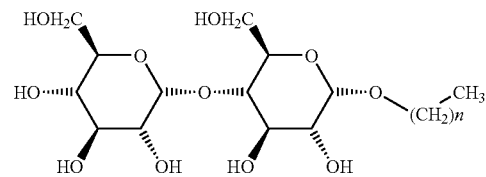

wherein n is 11.

4. The method of claim 1, wherein the pretreatment composition comprises about 0.025 to about 0.4% by weight of the transduction enhancing agent.

5. The method of claim 1, wherein the luminal surface of the bladder is contacted with the pretreatment composition for at least 20 minutes.

6. The method of claim 1, wherein the luminal surface of the bladder is contacted with the composition comprising the replication competent oncolytic virus for 15 minutes or less.

7. The method of claim 1, wherein the luminal surface of the bladder is contacted with the composition comprising the replication competent oncolytic virus for 10 minutes or less.

8. The method of claim 1, wherein the transduction enhancing agent has the chemical formula:

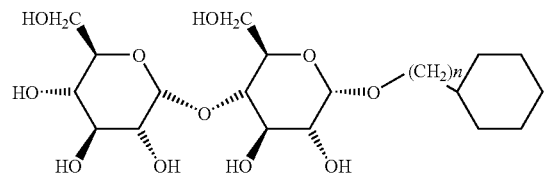

wherein n is 6.

9. The method of claim 1, wherein the oncolytic virus is an oncolytic adenovirus.

10. The method of claim 9, wherein the oncolytic adenovirus is CG8840.

11. The method of claim 1, wherein the oncolytic virus composition comprises at least $4 \times 10^{10}$ viral particles.

12. A method for transducing bladder epithelium cells, comprising:
   contacting the luminal surface of the bladder with a pretreatment composition comprising a transduction enhancing agent; and
   subsequently contacting the luminal surface of the bladder with a composition comprising a replication competent adenovirus;
   wherein the transduction enhancing agent has the following general formula (I):

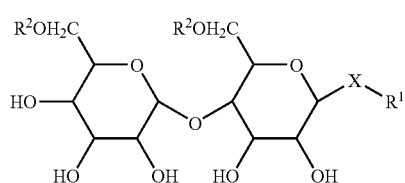
(I)

wherein X is an oxygen atom, and each $R^2$ is independently hydrogen or a moiety represented by:

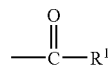

wherein $R^1$ represents an alkyl or alkenyl group of 12 carbons.

13. The method of claim 12, wherein each $R^2$ is hydrogen.

14. The method of claim 12, wherein the transduction enhancing agent has the chemical formula:

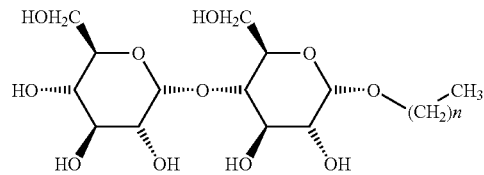

wherein n is 11.

15. The method of claim 14, wherein the pretreating composition comprises about 0.025 to about 0.4% by weight of the transduction enhancing agent.

16. The method of claim 12, wherein the transduction enhancing agent has the chemical formula:

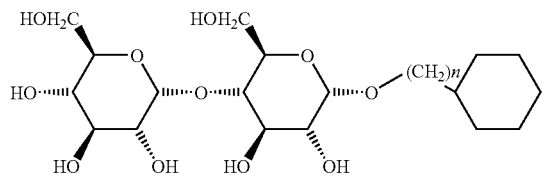

wherein n is 6.

17. The method of claim 1, wherein the luminal surface of the bladder is contacted with a pretreatment composition comprising a transduction enhancing agent and a replication competent adenovirus at the same time.

18. The method of claim 1, wherein the luminal surface of the bladder is contacted with a pretreatment composition comprising a transduction enhancing agent prior to contact with a replication competent adenovirus.

* * * * *